United States Patent
Van Dalen et al.

(10) Patent No.: US 9,295,583 B2
(45) Date of Patent: Mar. 29, 2016

(54) ANTERIOR CAPSULOTOMY DEVICE AND PROCEDURE

(71) Applicant: Eye Care and Cure Asia Pte Ltd, Singapore (SG)

(72) Inventors: Johan T. W. Van Dalen, Tucson, AZ (US); Dan D. Carda, Tucson, AZ (US)

(*) Notice: Subject to any disclaimer, the term of this patent is extended or adjusted under 35 U.S.C. 154(b) by 170 days.

(21) Appl. No.: 13/831,614

(22) Filed: Mar. 15, 2013

(65) Prior Publication Data

US 2013/0274755 A1  Oct. 17, 2013

Related U.S. Application Data

(63) Continuation-in-part of application No. PCT/US2012/030758, filed on Mar. 27, 2012.

(51) Int. Cl.
    *A61F 9/007* (2006.01)
(52) U.S. Cl.
    CPC ......... *A61F 9/00754* (2013.01); *A61F 9/00763* (2013.01)
(58) Field of Classification Search
    CPC ........ A61B 17/14; A61F 9/007; A61F 9/0074
    USPC .......................................... 606/107, 166, 167
    See application file for complete search history.

(56) References Cited

U.S. PATENT DOCUMENTS

| | | | |
|---|---|---|---|
| 2,249,906 A | 7/1941 | Longoria | |
| 3,756,128 A | 9/1973 | Armstrong et al. | |
| 5,261,923 A | 11/1993 | Soars | |
| 5,342,377 A | 8/1994 | Lazerson et al. | |
| 5,423,841 A | 6/1995 | Kornfeld | |
| 5,522,829 A | 6/1996 | Michalos | |
| 5,591,185 A | 1/1997 | Kilmer et al. | |
| 5,860,994 A | 1/1999 | Yaacobi | |
| 6,165,190 A | 12/2000 | Nguyen | |
| 6,506,176 B1 * | 1/2003 | Mittelstein et al. | 604/22 |
| 8,142,459 B2 | 3/2012 | Van Dalen | |
| 2004/0092982 A1 | 5/2004 | Sheffer | |
| 2004/0116950 A1 | 6/2004 | Eibschitz-Tsimhoni | |
| 2011/0029005 A1 | 2/2011 | Van Dalen et al. | |
| 2011/0264130 A1 | 10/2011 | Glazer et al. | |

FOREIGN PATENT DOCUMENTS

DE          10220253         11/2002

OTHER PUBLICATIONS

PCT/US2010/043584—International Search Report and Written Opinion dated Sep. 16, 2010.
PCT/US2012/030758—International Search Report and Written Opinion dated Aug. 3, 2012.
PCT/US2014/030771—International Search Report and Written Opinion dated Aug. 21, 2014.
PCT/US2012/030758—International Preliminary Report on Patentability dated Oct. 1, 2014.
International Preliminary Report on Patentability dated Sep. 24, 2015 for International Application No. PCT/US2014/030771.

* cited by examiner

*Primary Examiner* — Jonathan W Miles
*Assistant Examiner* — George J Ulsh
(74) *Attorney, Agent, or Firm* — Dale F. Regelman; Quarles & Brady LLP

(57) ABSTRACT

A device 1500 for performing an anterior capsulotomy procedure, wherein the device includes a body 1504 having proximal and distal ends. A cutting element 1010 having at least one surgical blade 1014 is rotatably disposed on a distal end of the body. The cutting element is attached to a pinion 1300 comprising a plurality of gear teeth 1310. The gear teeth on the pinion intermesh with gear teeth 1204 disposed on a distal end of a shaft assembly 1202. As the shaft assembly 1202 is moved laterally within the body 1504, the pinion 1300 is caused to rotate.

17 Claims, 25 Drawing Sheets

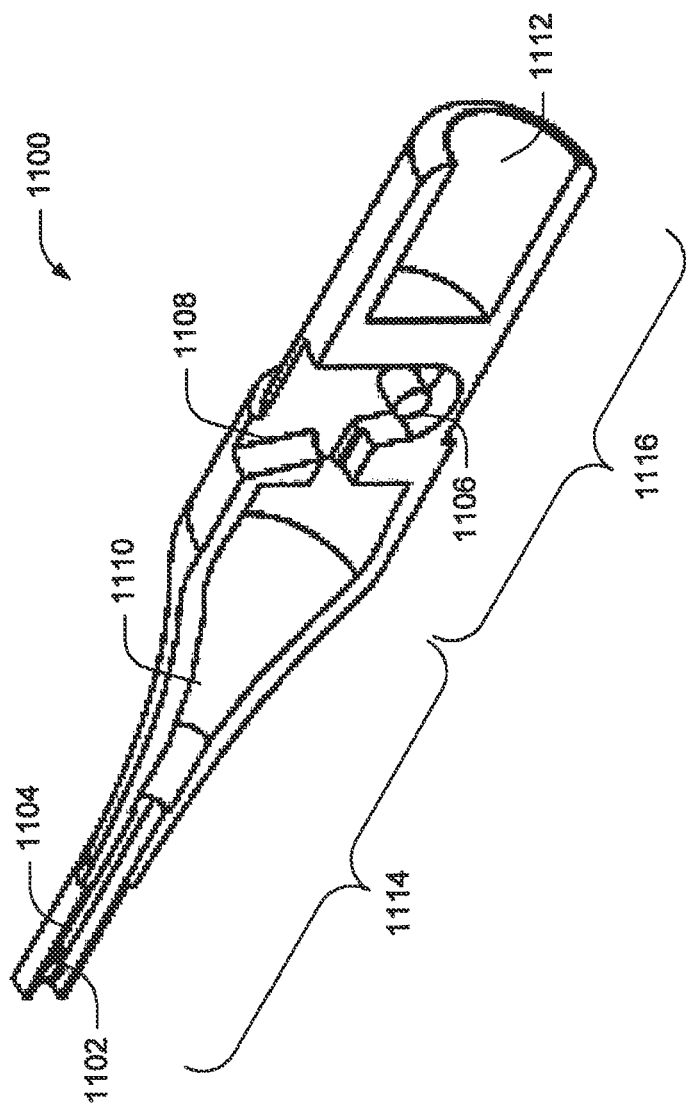

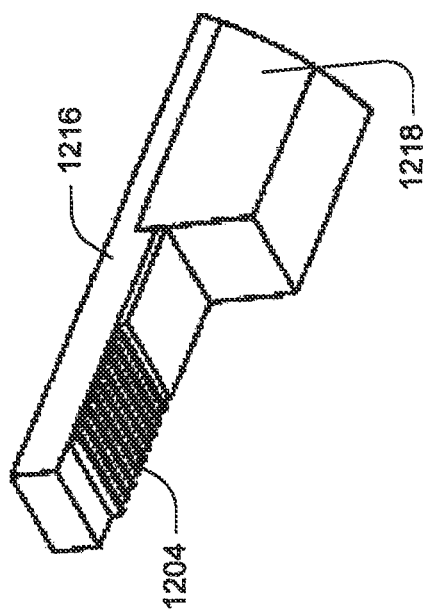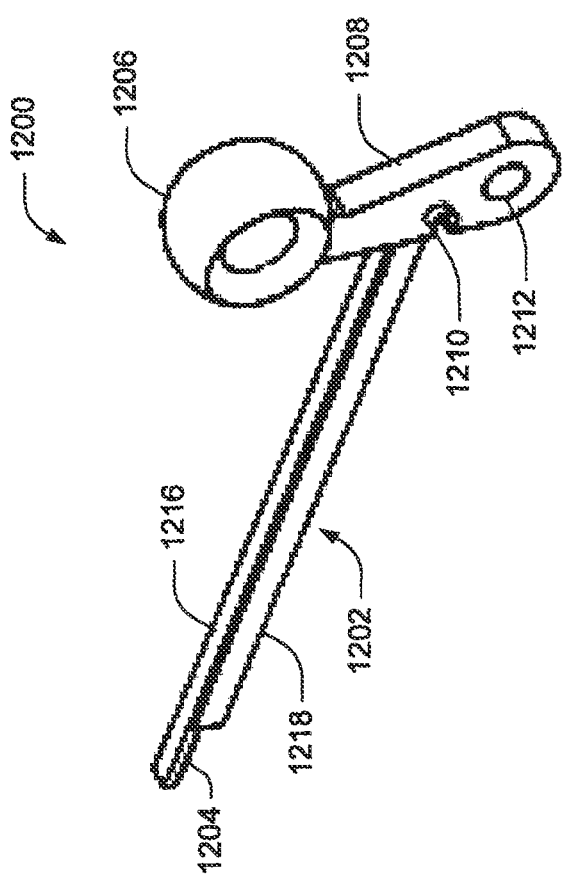
FIG. 12B
FIG. 12A

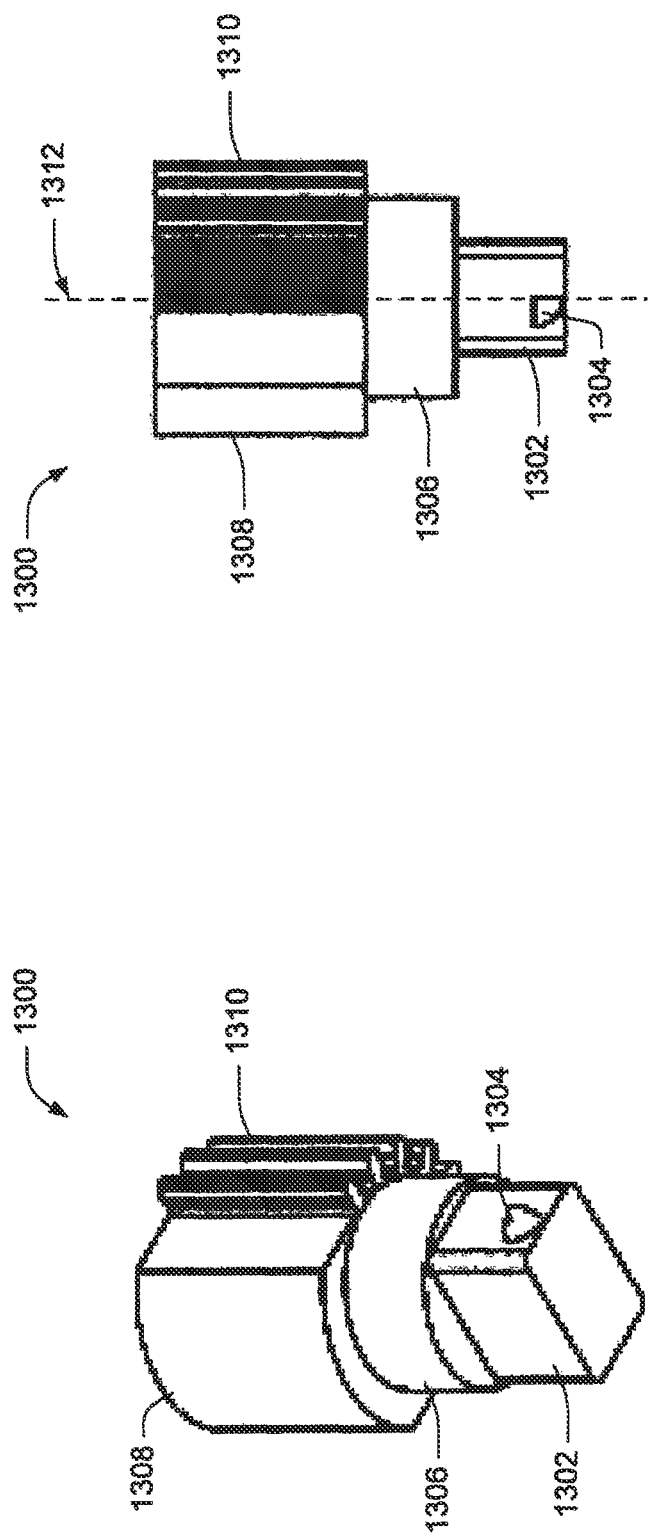

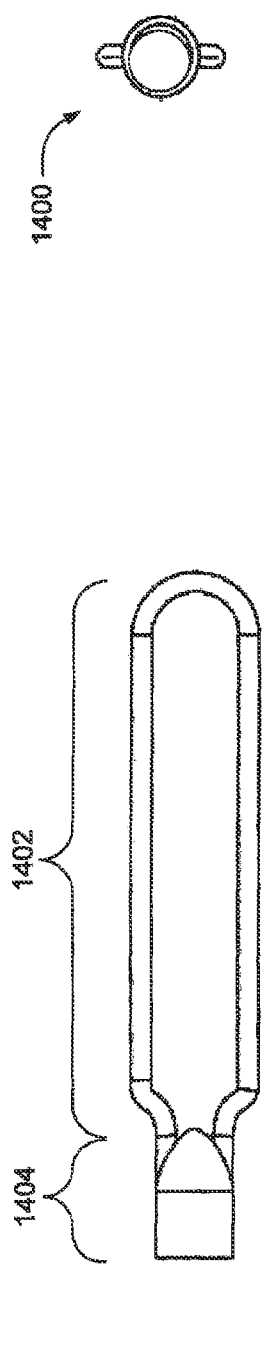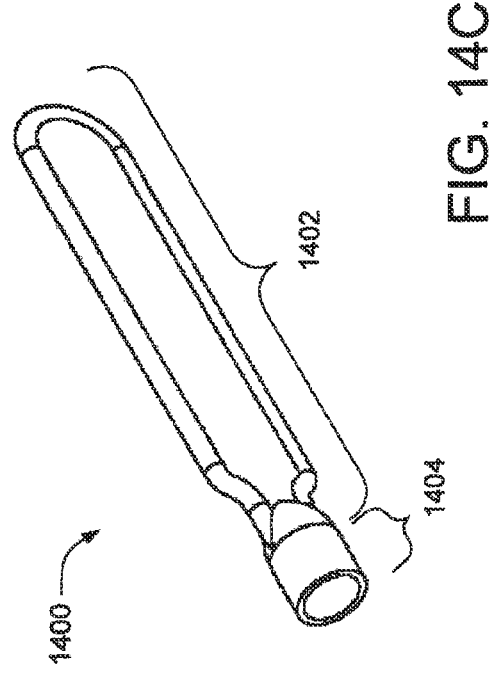

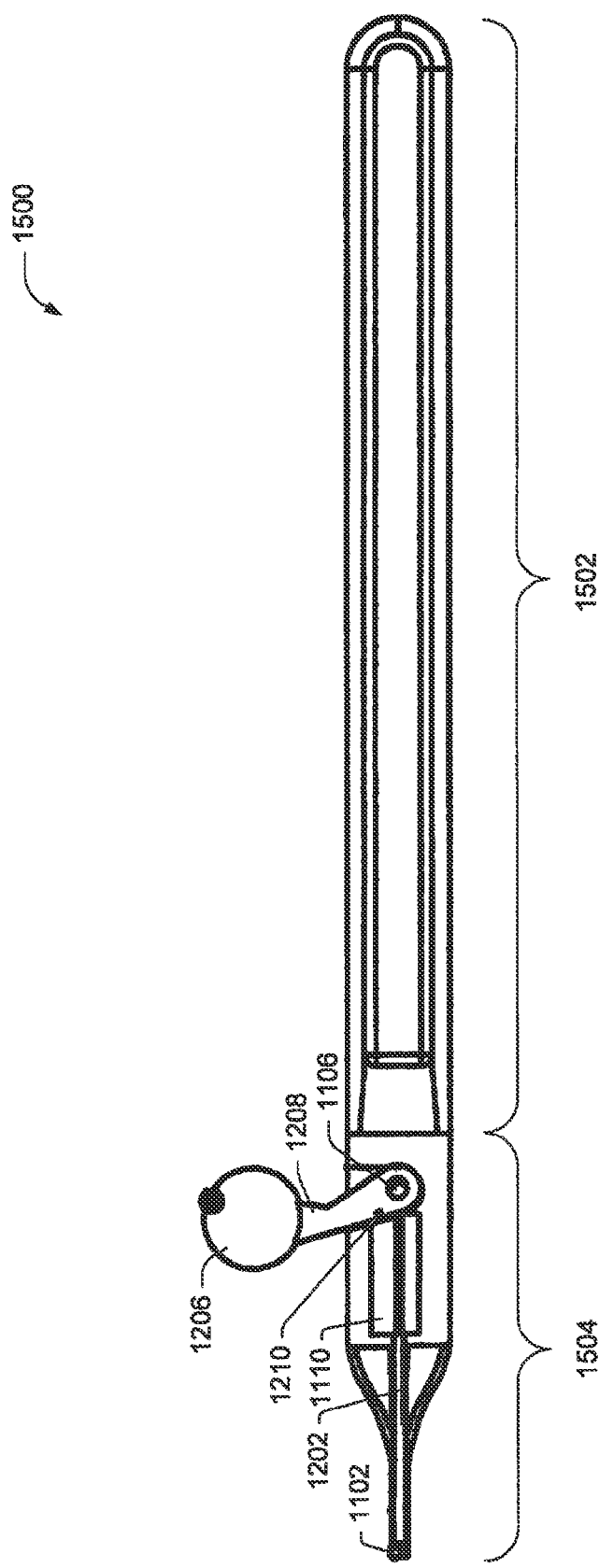

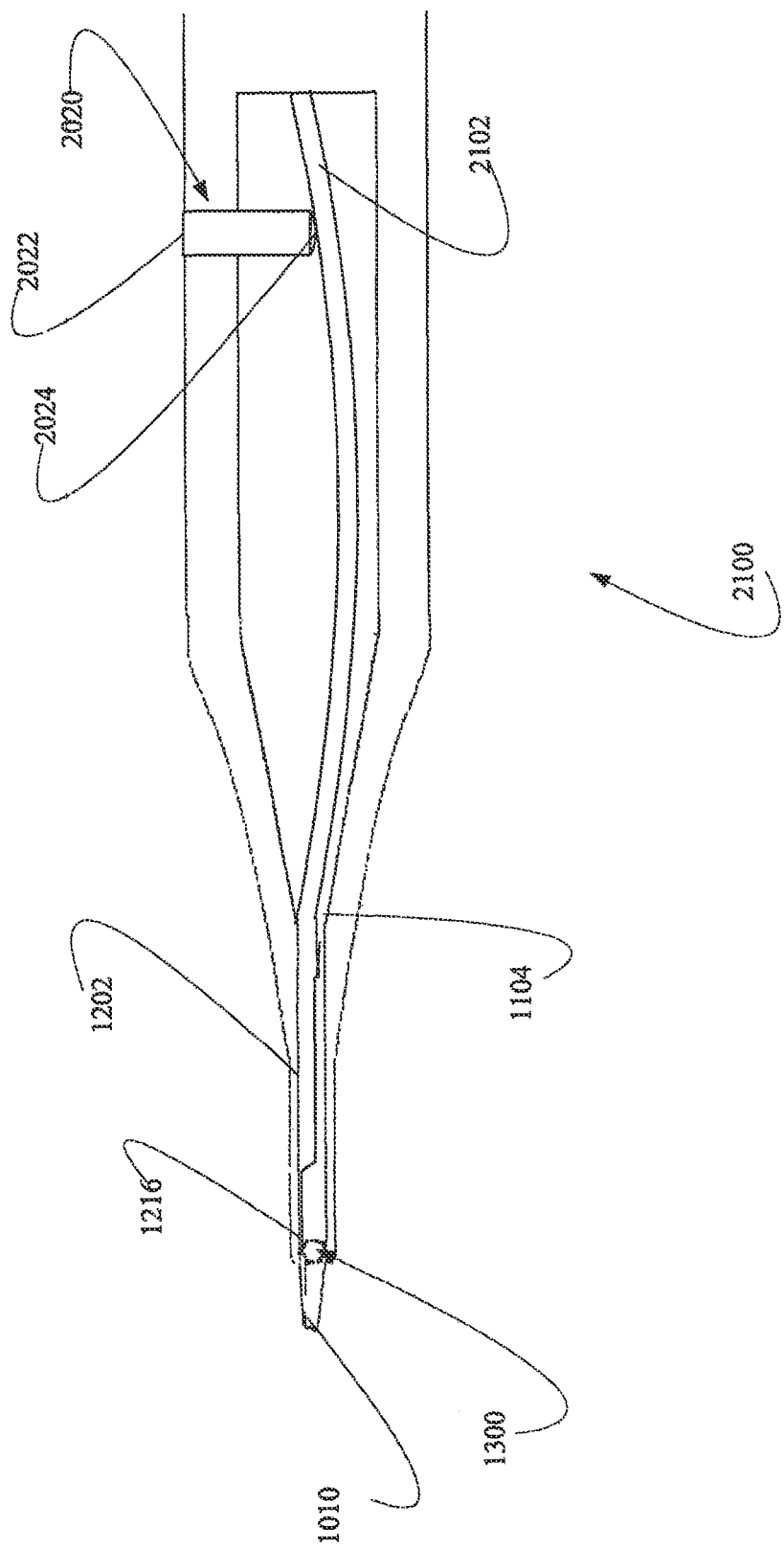

ANTERIOR CAPSULOTOMY DEVICE AND PROCEDURE

CROSS-REFERENCE TO RELATED APPLICATIONS

This Application is a Continuation-In-Part application claiming priority to a PCT Application filed on Mar. 27, 2012 with the United States Patent and Trademark Office, and having International No. PCT/US2012/030758, and which hereby is incorporated by reference.

BACKGROUND

The present invention relates generally to medical devices and more particularly to medical devices for performing an anterior capsulotomy (capsulorrhexis).

During cataract surgery, or removal and replacement of the natural lens of the eye, a surgeon must enter the globe, using a small millimeter blade, to access the cataract, which commonly involves the centermost layer (the cortex) of the lens. Most often, a clear corneal suture-less incision of 3 mm or less is made. The anterior chamber is then filled with a viscoelastic substance to protect the cornea during cataract surgery and to maintain the integrity of the anterior chamber when necessary. An additional incision called a paracentesis is placed at approximately 90° (ninety degrees) to facilitate the manipulation of the cataract during phaco emulsification, a process that utilizes ultrasound to gently suction out the cataract.

Prior to the suctioning of the cataract, an opening in the capsule is needed to allow for the use of devices required to effectively remove cortex and nucleus from the capsule. It is of the utmost importance that the integrity of the anterior (after anterior capsulotomy) and posterior capsule is maintained. Post-operatively the capsular envelope serves as a retainer for an artificial implant (intra-ocular lens (IOL). Without the capsule, or if the structure is compromised, the use of a posterior implant may be contraindicated since the capsule provides the support needed to keep the artificial lens in place.

There are two prior art methods of performing an anterior capsulotomy. The first, referred to as the "can opener" technique, is an older procedure before more modern techniques and advanced equipment (such as the Utrata forceps) became available. This procedure involves the surgeon making a series of small, connected punctures using a cystotome, or bent needle, running 360° (three-hundred and sixty degrees) around the anterior portion of the capsule, resulting in an opening that resembles the appearance of the top of an open can.

The second method requires the surgeon to nick the anterior portion of the capsule with a cystotome to create a tear in the membrane. Using an Utrata forceps, an edge of the tear is grasped and guided to create a circular aperture in the surface of the anterior capsule.

Both techniques require significant skill on the part of the surgeon and generally take years to master. Even a slight error, can result in a devastating prognosis for the patient. If the capsulotomy is too small, the cataract may not be removed sufficiently, If the capsulotomy is too large or the anterior capsule tears during the process, extending and resulting in a posterior capsular tear, the capsule may not be able to support the artificial lens implant or, worse yet, there may be a loss of the vitreous. If a vitreous loss occurs an immediate vitrectomy is required, which has the potential of a lifetime of visual impairment or blindness for the patient. Furthermore, the use of many newer intraocular lenses require that the anterior capsulotomy be performed such that a circular opening with a predetermined diameter be made.

Thus, the prior art methods for performing anterior capsulotomies possess inherent deficiencies that increase the likelihood of complications and decrease the procedure's safety. Therefore, there is a need for a means of reliably and safely performing an anterior capsulotomy.

SUMMARY

In one implementation, a device for performing an anterior capsulotomy procedure is presented. The device includes a body having proximal and distal ends. A cutting element having at least one surgical blade is rotatably disposed on a distal end of the body. The cutting element is attached to a pinion comprising a plurality of gear teeth. The gear teeth on the pinion intermesh with gear teeth disposed on a distal end of a shaft assembly. As the shaft assembly is moved laterally within the body, the pinion is caused to rotate.

In another implementation, the cutting element of the device further includes an arcuate member having opposing first and second ends. A first surgical blade is attached to, or part of, the first end and a second surgical blade is attached to, or part of, the second end, the surgical blades extending outwardly from the arcuate member.

In another implementation, a method of performing an anterior capsulotomy is presented. The method includes making an incision in an eye. The method further includes inserting a proximal end of Applicants' device into the incision, bringing the at least one surgical blade in contact with an anterior capsule wall, moving an actuator from a first position to a second position to create an aperture in the anterior capsule wall.

BRIEF DESCRIPTION OF THE DRAWINGS

Implementations of the invention will become more apparent from the detailed description set forth below when taken in conjunction with the drawings, in which like elements bear like reference numerals.

FIG. 11 is a cutaway perspective view of the body of an exemplary anterior capsulotomy device using a rack and pinion mechanism;

FIG. 12A is a perspective view of an exemplary rack mechanism for use in the anterior capsulotomy device body of FIG. 11;

FIG. 12B is a close up view of one portion of the rack mechanism of FIG. 12A;

FIG. 13A is a perspective view of a pinion used in certain embodiments of an anterior capsulotomy device;

FIG. 13B is a side view of the pinion of FIG. 13A;

FIGS. 14A, 14B, and 14C are different views of an exemplary handle for use with an anterior capsulotomy device;

FIG. 15 shows a side view of Applicants' anterior capsulotomy device 1500;

FIG. 21B shows a cross-section view of Applicants' anterior capsulotomy device 2100, wherein actuator 2020 is disposed in a second position;

DETAILED DESCRIPTION

This invention is described in preferred embodiments in the following description with reference to the Figures, in which like numbers represent the same or similar elements. Reference throughout this specification to "one embodiment," "an embodiment," or similar language means that a particular feature, structure, or characteristic described in connection with the embodiment is included in at least one embodiment of the present invention. Thus, appearances of the phrases "in certain embodiments," "in an embodiment," and similar language throughout this specification may, but do not necessarily, all refer to the same embodiment.

The described features, structures, or characteristics of the invention may be combined in any suitable manner in one or more embodiments. In the following description, numerous specific details are recited to provide a thorough understanding of embodiments of the invention. One skilled in the relevant art will recognize, however, that the invention may be practiced without one or more of the specific details, or with other methods, components, materials, and so forth. In other instances, well-known structures, materials, or operations are not shown or described in detail to avoid obscuring aspects of the invention.

The anterior capsulotomy device of the present invention is illustrated in FIGS. 5-9. For illustrative purposes only, FIGS. 1-4 are provided depicting the prior art methodology.

Figure 1:
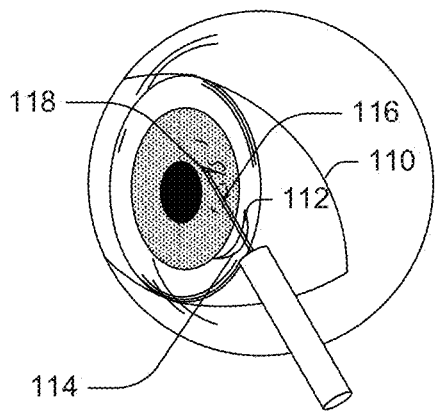
FIG. 1 is a prospective view of a human eyeball illustrating the prior art practice of performing an anterior capsulotomy.

Referring now to FIG. 1, a human eye 110 is depicted having an anterior capsule 122 (FIG. 3) exposed through the pupil 128 of the overlying iris 132, and the sclera 130 (FIG. 4) circumferentially surrounding iris 132. The cornea 114 overlies anterior capsule 122, pupil 128, and iris. Historically, an anterior capsulotomy is performed by making an initial limbal incision 112 in the limbus zone where sclera and iris meet. Alternatively, a clear corneal incision may be made instead.

Figure 2:
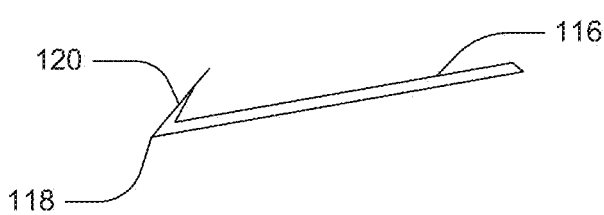
FIG. 2 is an exemplary stylet or needle used to perform an anterior capsulotomy according to the prior art method.
Figure 3:
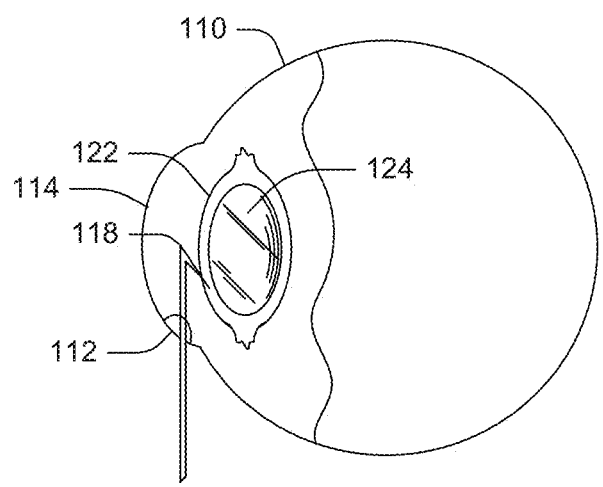
FIG. 3 is a cross-sectional view of a human eyeball further illustrating the prior art method of performing an anterior capsulotomy.
Figure 4:
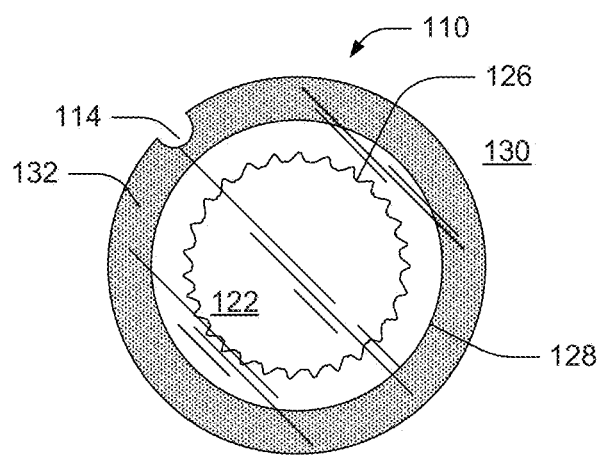
FIG. 4 is a front view of a cornea after an anterior capsulotomy is performed according to the prior art method.

As further depicted in FIG. 2, a stylet or needle 116 having a bend 118 such that the head 120 of stylet or needle 116 can be inserted through incision 112. As can be seen in FIG. 3, head 120 of stylet or needle 116 is then used to make small, overlapping tears in anterior capsule 122 to form an opening that can be used to remove the original lens 124 and insert an artificial one. Specifically, the process requires the repeated puncturing of anterior capsule 122 with head 120 of stylet or needle 116 and pulling on the stylet or needle 116, each time making small tear in the anterior capsule 122. As shown in FIG. 4, this repeated tearing of anterior capsule 122 forms a jagged opening 126 in anterior capsule 122.

Figure 5A:
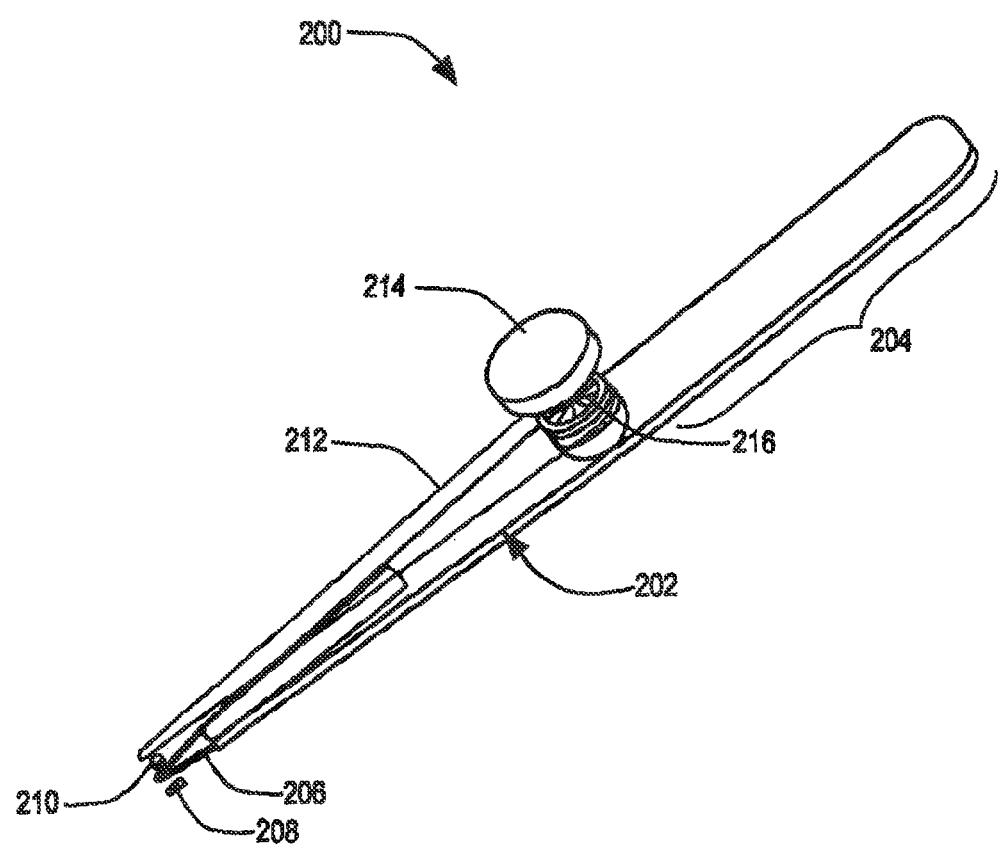
FIG. 5A is a perspective view of an exemplary anterior capsulotomy device of the present invention.
Figure 5B:
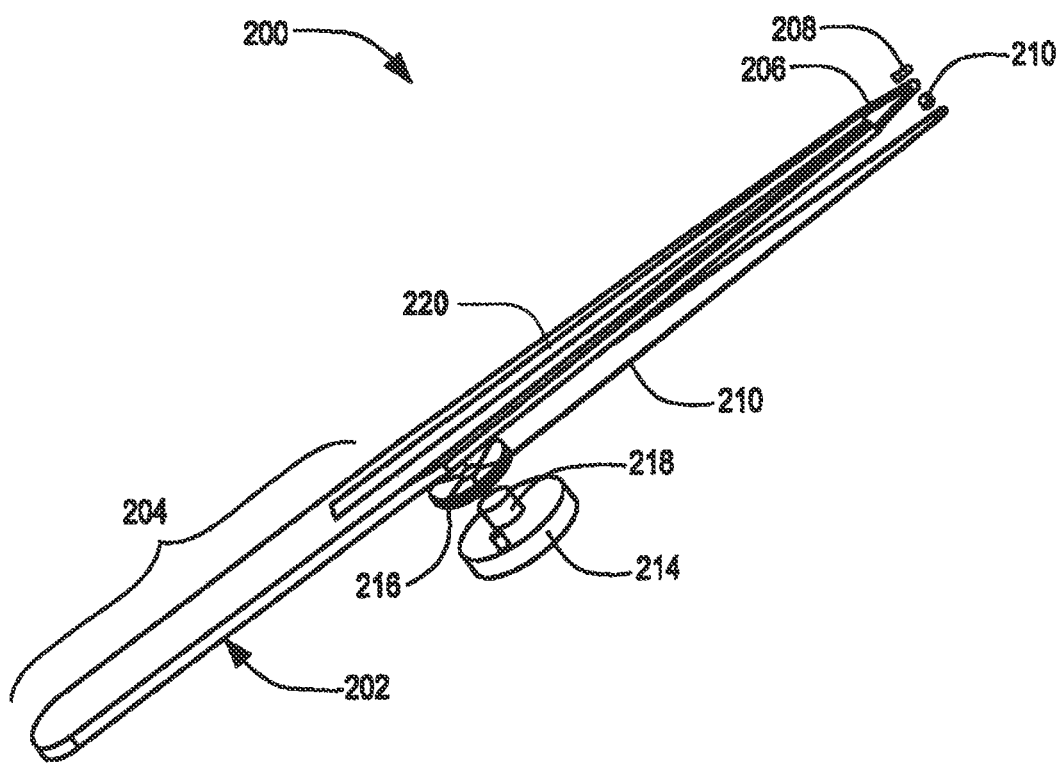
FIG. 5B is a perspective view of the underside of the exemplary anterior capsulotomy device of FIG. 5A.

With the foregoing background information, the operation and utility of the instrument of the present invention may now be explained and fully understood. Referring now to FIGS. 5A and 5B, the anterior capsulotomy device 200 of the present invention generally comprises a body 202, wherein the proximal end is tapered to a head 206 and the distal end acts as a handle portion 204. Device 200 further comprises a front pulley 210 connected to a cutting element 208, wherein a portion of front pulley 210 extends through an opening in head 206 to attach to cutting element 208.

Actuator 214 is attached to body 202 such that actuator 214 can be moved by a thumb of a user. Actuator 214 is connected to rear pulley 216 via connecting element 218 (FIG. 5B only) such that, when moved, actuator 214 causes rear pulley 216 to rotate. Rear pulley 216 is in turn connected to front pulley 210 by connecting element 212, such that rotation of rear pulley 216 causes rotation of front pulley 210 and cutting element 208.

In certain embodiments, connecting element 212 comprises a continuous assembly. In certain embodiments, connecting element 212 comprises a cable. In other embodiments, connecting element 212 comprises a belt. In yet other embodiments, connecting element 212 comprises a cord. In certain embodiments, connecting element 212 is formed from a plastic. In other embodiments, connecting element 212 comprises a metal.

As depicted in FIGS. 5A and 5B, actuator 214 is mechanically operated by a thumb of a user. In certain embodiments, actuator 214 is rotated by the user. In other embodiments, actuator 214 is depressed by the user. As will be clear to one of ordinary skill in the art, other types of actuators may be used in place of actuator 214 without departing from the scope of the disclosure.

In the illustrated embodiment of FIG. 5B, body 202 is illustrated as being formed to include groove 220. In other embodiments, anterior capsulotomy device 200 is not formed to include such a groove.

Figure 6:
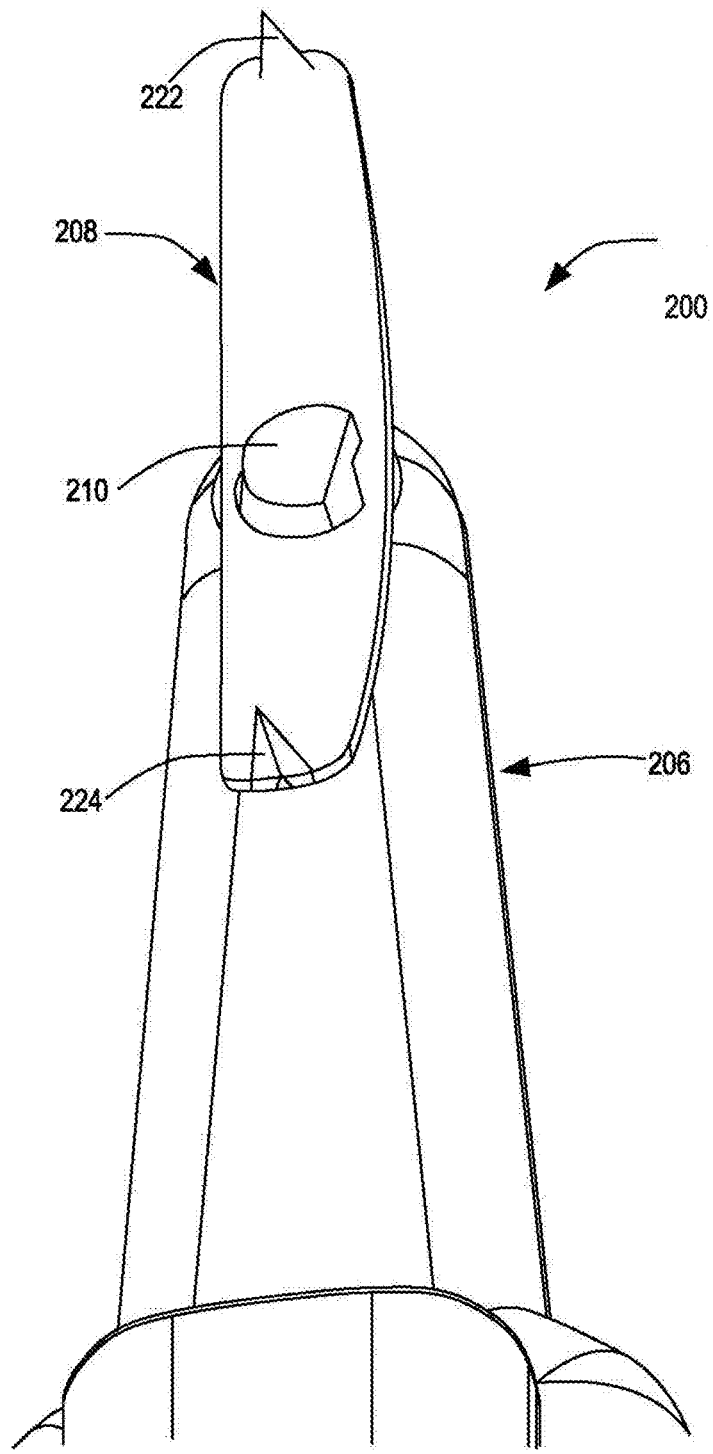
FIG. 6 is a detailed view of the head of the exemplary anterior capsulotomy device of FIG. 5A.
Figure 7:
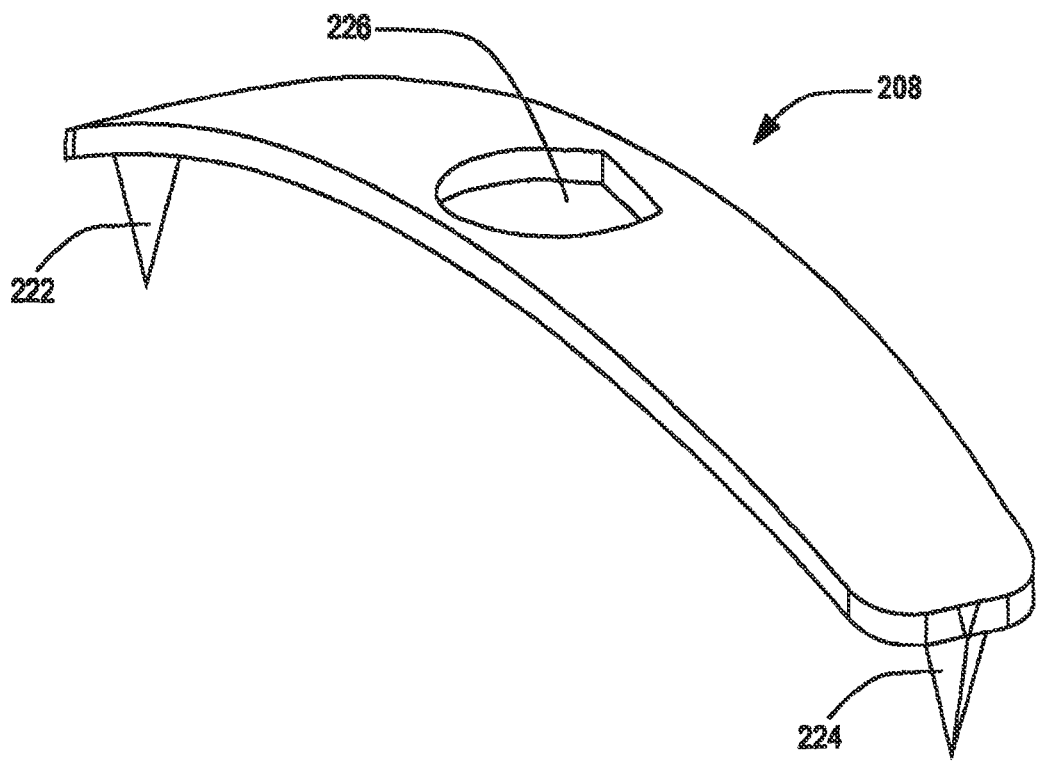
FIG. 7 is a detailed view of the cutting element of the exemplary anterior capsulotomy device of FIG. 5A.

Referring now to FIGS. 6 and 7, cutting element 208 is rotatably disposed on head 206 and is attached thereto by front pulley 210. Member 408 (FIG. 8) is attached to front pulley 210, and extends through head 206, and couples to the periphery of aperture 226 (FIG. 7) formed in cutting element 208, thereby securing cutting element 208 to head 206 while allowing cutting element 208 to rotate with front pulley 210.

In the illustrated embodiments of FIGS. 6 and 7, cutting element 208 comprises two (2) surgical blades, namely blade 222 and blade 224, disposed on opposite ends of cutting element 208 and projecting in a downward direction. In certain embodiments, blades 222 and 224 are formed on cutting element 208 such that cutting element 208 and blades 222 and 224 are a single, contiguous formation. In other embodiments, blades 222 and 224 are disposed on cutting element 208.

In certain embodiments, only the leading edges of blades 222 and 224 are cutting edges. In other embodiments, both the leading and trailing edges of blades 222 and 224 are cutting edges. In such an embodiment, cutting element 208 may be rotated in either a clockwise or counterclockwise direction without affecting the device's ability to cut the anterior capsulotomy.

In certain embodiments, blades 222 and 224 comprise one or more metals. In certain embodiments, blades 222 and 224 comprise the same substance as cutting element 208. In yet other embodiments, blades 222 and 224 comprise a different substance than cutting element 208.

Figure 8:
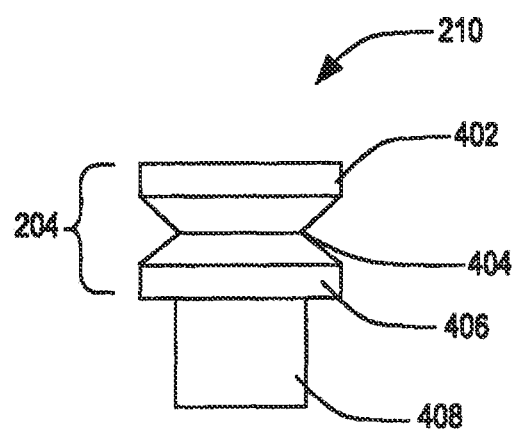
FIG. 8 is a detailed view of the front pulley of the exemplary anterior capsulotomy device of FIG. 5A.
Figure 9A:
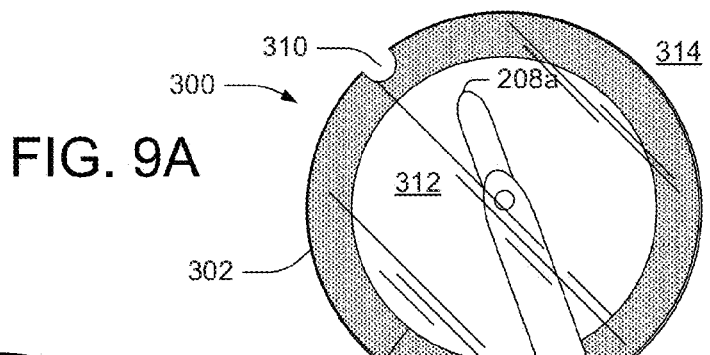
FIG. 9A depicts the insertion of the exemplary anterior capsulotomy device of FIG. 5A in a limbal incision.
Figure 9B:
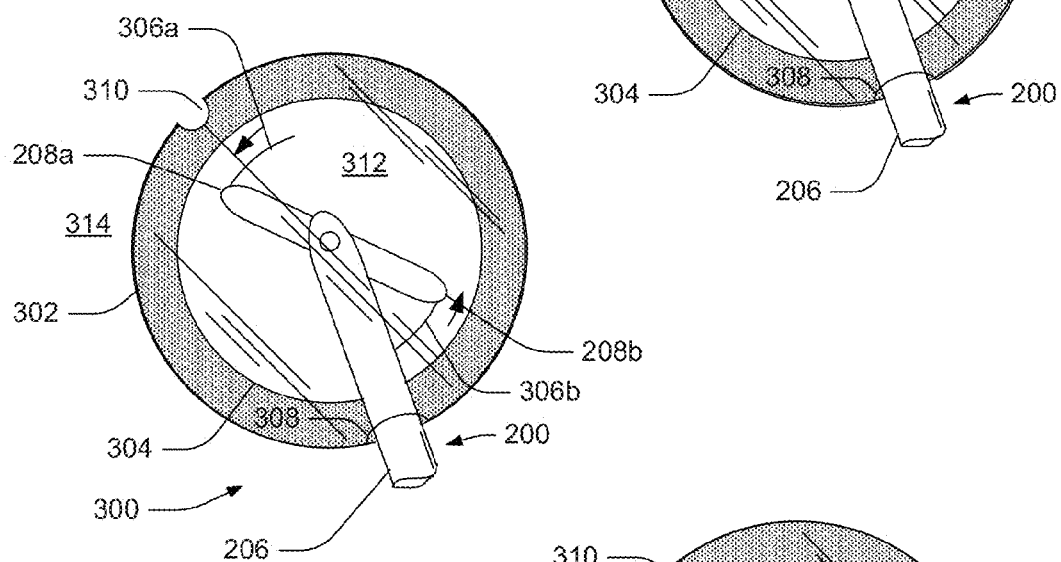
FIG. 9B depicts the process of making an incision in the anterior capsulotomy using the exemplary anterior capsulotomy device of FIG. 5A.
Figure 9C:
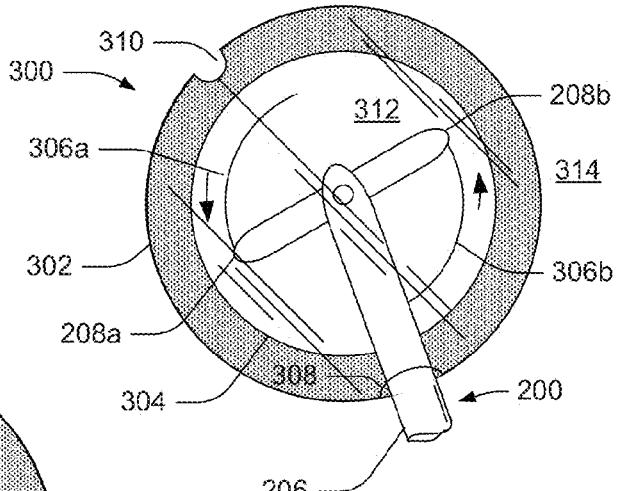
FIG. 9C provides another view of the process of making an incision in the anterior capsulotomy using the exemplary anterior capsulotomy device of FIG. 5A.
Figure 9D:
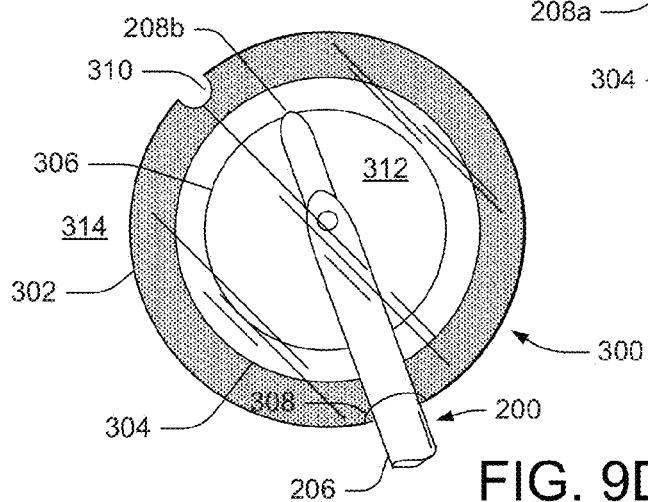
FIG. 9D depicts the completion of a circular incision in the anterior capsulotomy made using the exemplary anterior capsulotomy device of FIG. 5A.

Turning to FIG. 8, the exemplary embodiment of front pulley 210 is shown as having member 408, which extends through head 206 (FIGS. 5A, 5B, and 6) and aperture 226 (FIG. 7) to secure cutting element 208 (FIGS. 5A, 5B, 6, and 7) to head 206. As will be understood by one of ordinary skill in the art, cutting element 208 may be rotatably attached to head 206 by a means other than front pulley 210 without departing from the scope of the disclosed invention.

In certain embodiments, front pulley 210 is formed such that member 408 is substantially cylindrical having one flat side (illustrated in FIG. 6) that abuts a flat side of aperture 226 (FIG. 7). In other embodiments, member 408 and aperture 226 may have other configurations.

As illustrated in FIG. 8, front pulley 210 additionally comprises sheave 410 formed to include groove 404 disposed between upper flange 402 and lower flange 406 along the circumference of sheave 410. When connecting cutting element 208 (FIGS. 5A, 5B, 6, and 7) to head 206 (FIGS. 5A, 5B, and 6), lower flange 406 rests on top of head 206 while member 408 extends through head 206 and into aperture 226 (FIG. 7). Connecting element 212 (FIGS. 5A and 5B) then rests within groove 404.

One feature of the present invention is that the cutting element does not need to make a full 360 degree rotation when actuated by the actuator. Rather, the cutting element can make a circular incision by being rotated about 180 degrees. In certain embodiments, the cutting element comprises two blades, such as blades 222 and 224 (FIGS. 6 and 7), located at opposing ends of the cutting element. In these embodiments, the rotation causes each blade to make a contiguous semicircle incision of a predetermined diameter. In certain embodiments, the cutting element is rotated more than 180 degrees, and therefore, the ends of each semicircle overlap to form a single, circular incision.

The amount of the overlap is small to prevent and/or minimize tearing of the anterior capsulotomy in the area of the overlap. As is known by one of ordinary skill in the art, repeatedly cutting the same area of the anterior capsule wall increases the likelihood of tearing. In certain embodiments, the arcs cut by each blade of the cutting element overlap by two (2) degrees at either end. In such an embodiment, the cutting element rotates 182 degrees when actuated.

As will be clear to one of ordinary skill in the art, by having two opposing surgical blades, the overall sheer stress experienced by the anterior capsule wall is minimal compared to the sheer stress created by a cutting instrument having a single blade. As is known by one of ordinary skill in the art, sheer stress causes deformation of a material by slippage along a plane parallel and/or tangential to the imposed stress. This deformation increases the likelihood that the anterior capsule wall will tear. By utilizing two surgical blades, each moving in opposite directions at the same time and applying the same stress, each blade generates a sheer stress of equal value in opposing directions, thereby theoretically resulting in a net sheer stress of zero. As will be understood by one of ordinary skill in the art, the natural presence of imperfections, varying thickness, etc. will result in an actual net sheer stress that is slightly greater than zero.

As will be apparent to one of ordinary skill in the art, the diameter of the cut made by the cutting element is equal to the distance between the two blades. In certain embodiments, this distance is adjustable. In other embodiments, the disclosed anterior capsulotomy device may come in varying sizes, each having a different distance between the blades. Alternatively, the cutting head may be interchangeable; different cutting heads having blades spaced different lengths apart.

Turning now to FIGS. 9A-9D, the manner of performing a capsulotomy using the present invention is illustrated. Each of the FIGs. depict a human eye 300 having an anterior capsule 312 exposed through the pupil 304 of the overlying iris 302, and the sclera 314 circumferentially surrounding iris 302. The cornea 310 overlies anterior capsule 312, pupil 304, and iris 302. Initially, head 206 of the disclosed device is inserted through a small limbal incision 308 and the cutting element is placed in contact with the wall of the anterior capsule 312. In certain embodiments, head 206 is alternatively inserted through a clear corneal incision. By using the actuator (not shown), the cutting element is rotated in the manner depicted in FIGS. 9B-9D. The blades at ends 208a and 208b of the cutting element cut opposing arcs 306a and 306b, shown in FIGS. 9B and 9C. As discussed, the cutting element makes a slightly greater then 180 degree rotation thereby causing arcs 306a and 306b to overlap, forming circular opening 306 shown in FIG. 9D. At this point, head 206 is withdrawn and the cut portion of the anterior capsulotomy wall may then be removed through limbal incision 308 using a probe or other device.

Figure 10A:
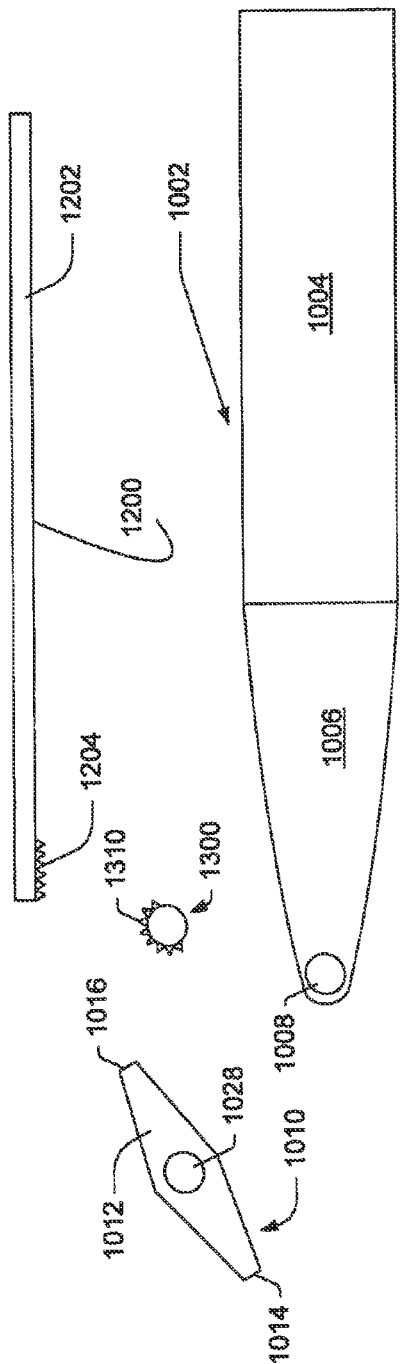
FIG. 10A is a block diagram showing the components of an exemplary anterior capsulotomy device having a rack and pinion mechanism.
Figure 10B:
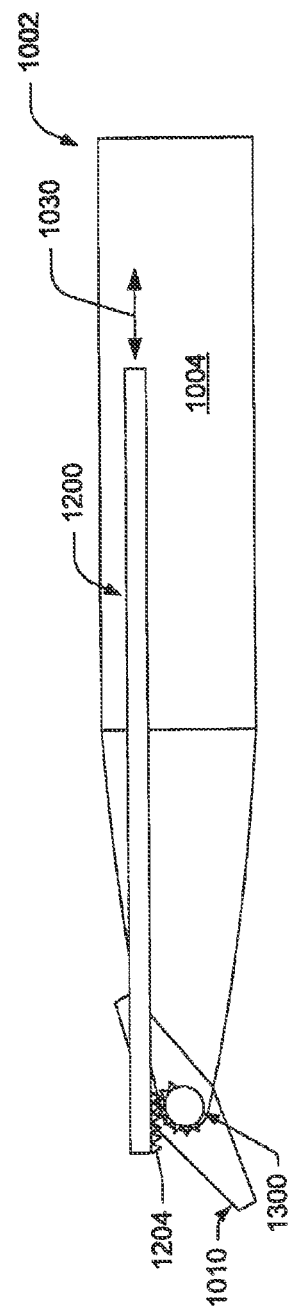
FIG. 10B is a block diagram showing the assembled components of the exemplary anterior capsulotomy device of FIG. 10A.

FIGS. 10A and 10B illustrate portions of Applicants' anterior capsulotomy device 1500 (FIG. 15). Many details have been omitted from the block diagrams in FIGS. 10A and 10B for the purpose of clarity. As such, the lack of a particular detail should not be viewed as limiting. In addition, other FIGs. discussed herein provide additional details omitted from FIGS. 10A and 10B.

Body 1100 includes a handle 1004 and an arm 1006. An aperture 1008 is formed in arm 1006. A blade assembly 1010 includes blade arm 1012. An aperture 1028 is formed in blade arm 1012. Surgical blades (not shown in FIG. 10A) are positioned at the ends 1014 and 1016 of blade arm 1012. Pinion 1300 includes gear teeth 1310. A rack assembly 1200 includes a shaft 1202 and gear teeth 1204.

Turning to FIG. 10B, blade assembly 1010 is attached to body 1100 via pinion 1300. Pinion 1300 extends outwardly from aperture 1008. The rack assembly 1200 is positioned within the body portion 1002 such that the gear teeth 1204 on the shaft 1202 intermesh with the gear teeth 1310 on the pinion 1300. Lateral movement of the shaft 1202 (as indicated by arrow 1030) will cause the blade assembly 1010 to rotate.

FIG. 11 shows body 1100 split longitudinally with one side removed for illustrative purposes. The body 1100 includes an upper handle portion 1116 and an arm 1114. Aperture 1008 is formed in the tip of the arm 1114. The aperture 1008 receives pinion 1300 which is connected to blade assembly 1010.

A channel 1104 is formed within arm 1114. The channel 1104 communicates with a first end of cavity 1110. A second end of cavity 1110 communicates with activation slot 1108. A pivot member 1106 is formed within activation slot 1108. A handle cavity 1112 is formed in the upper handle portion 1116 and is configured to receive an extended handle (not shown).

In certain embodiments, the body 1100 is formed from a metal. In certain embodiments, the body 1100 is formed from a liquid crystal polymer, such as ZENITE sold in commerce by Ticona LLC. In certain embodiments, the body is comprised from any material that can be sterilized using ethylene oxide sterilization, gamma irradiation, or autoclaving.

Referring to FIGS. 12A and 12B, rack assembly 1200 comprises a shaft 1202. In certain embodiments, shaft 1202 comprises horizontal member 1216 and support member 1218. The support member 1218 strengthens and stabilizes the horizontal member 1216. Gear teeth 1204 are formed on a distal end of horizontal member 1216. In certain embodiments the support member 1218 and the horizontal member 1216 are formed from different materials. In certain embodiments, the support member 1218 and the horizontal member 1216 are formed from the same material. In certain embodiments, the horizontal member 1216 is formed from metal or a liquid crystal polymer. In certain embodiments, the support member 1218 and the horizontal member 1216 are integrally formed. In different embodiments, the support member is formed from metal or a liquid crystal polymer.

Shaft 1202 is coupled to activation member 1208. End 1212 (FIG. 16) is inserted into aperture 1210. An aperture 1212 is formed in activation member 1208. In certain embodiments, activation member 1208 is formed from metal or a liquid crystal polymer. In certain embodiments, activation member 1208 is formed from metal or a liquid crystal polymer. FIG. 12B illustrates gear teeth 1204 disposed on, or integrally formed in, a distal end of horizontal member 1216.

Referring to FIGS. 11, 12A and 12B, shaft 1202 is disposed within channel 1104 and cavity 1110. Activation member 1208 is disposed within activation slot 1108 such that pivot member 1106 extends through aperture 1212. The top portion of activation member 1208 as well as the activation head 1206 extend outwardly from body 1100.

Activation member 1208 moves within the activation slot 1108 by pivoting about pivot member 1106. Rotational movement of activation member 1208 causes lateral movement of shaft 1202 within channel 1104. Gear teeth 1204 on horizontal member 1216 intermesh with gear teeth 1310 on pinion 1300. Lateral movement of the shaft 1202 causes rotational movement of pinion 1300.

Referring to FIGS. 13A and 13B, pinion 1300 includes a blade assembly mounting member 1302. Blade assembly mounting member 1302 includes mounting clips 1304. Blade assembly 1010 is attached to pinion 1300 by sliding blade assembly 1010 onto the blade assembly mounting member 1302 and over the mounting clips 1304. The mounting clips 1304 thereby retain the blade assembly on the pinion mounting member 1302.

Pinion 1300 includes rotation sleeve 1306. Rotation sleeve 1306 extends through aperture 1102 formed in body 1100 in FIG. 11.

Pinion 1300 includes a head 1308. Pinion head 1308 includes gear teeth 1310. In certain embodiments, gear teeth 1310 are disposed around a portion of the perimeter of the head 1308, such that the lateral motion of shaft 1202 will cause the pinion to rotate no more than 182 degrees. In certain embodiments, gear teeth 1310 are arranged around a portion of the perimeter of the head 1308, such that the lateral motion of the shaft 1202 will cause the pinion to rotate more than 182 degrees. In certain embodiments, gear teeth 1310 are arranged around the entire perimeter of the head 1308, such that lateral motion of the shaft 1202 will cause pinion 1300 to rotate 360 degrees.

Turning to FIG. 13B, dashed line 1312 corresponds to a rotational axis of the pinion 1300. In certain embodiments, gear teeth 1310 are disposed over more than one half of the periphery of pinion head 1308 to enable pinion 1300 to rotate about 182 degrees.

Referring to FIGS. 14A, 14B, and 14C, handle 1400 comprises connection adapter portion 1404 that tapers into a flat handle portion 1402. The adapter portion 1404 couples, in certain embodiments, to the handle adjacent cavity 1112 (see FIG. 11). FIG. 14B is an end view of the handle 1400. FIG. 14C is a perspective view of the handle 1400.

Referring to FIG. 15, Applicants' anterior capsulotomy device 1500 comprises a handle portion 1502 coupled to a head portion 1504. The head portion 1504 is shown in cross section. Aperture 1102 is formed in the tip of the head portion 1504. Channel 1104 is formed in the head portion 1504. Channel 1104 communicates with cavity 1110.

Activation member 1208 is rotationally disposed in the head portion 1504 about pivot member 1106. Activation head 1206 is connected to activation member 1208.

Figure 16:
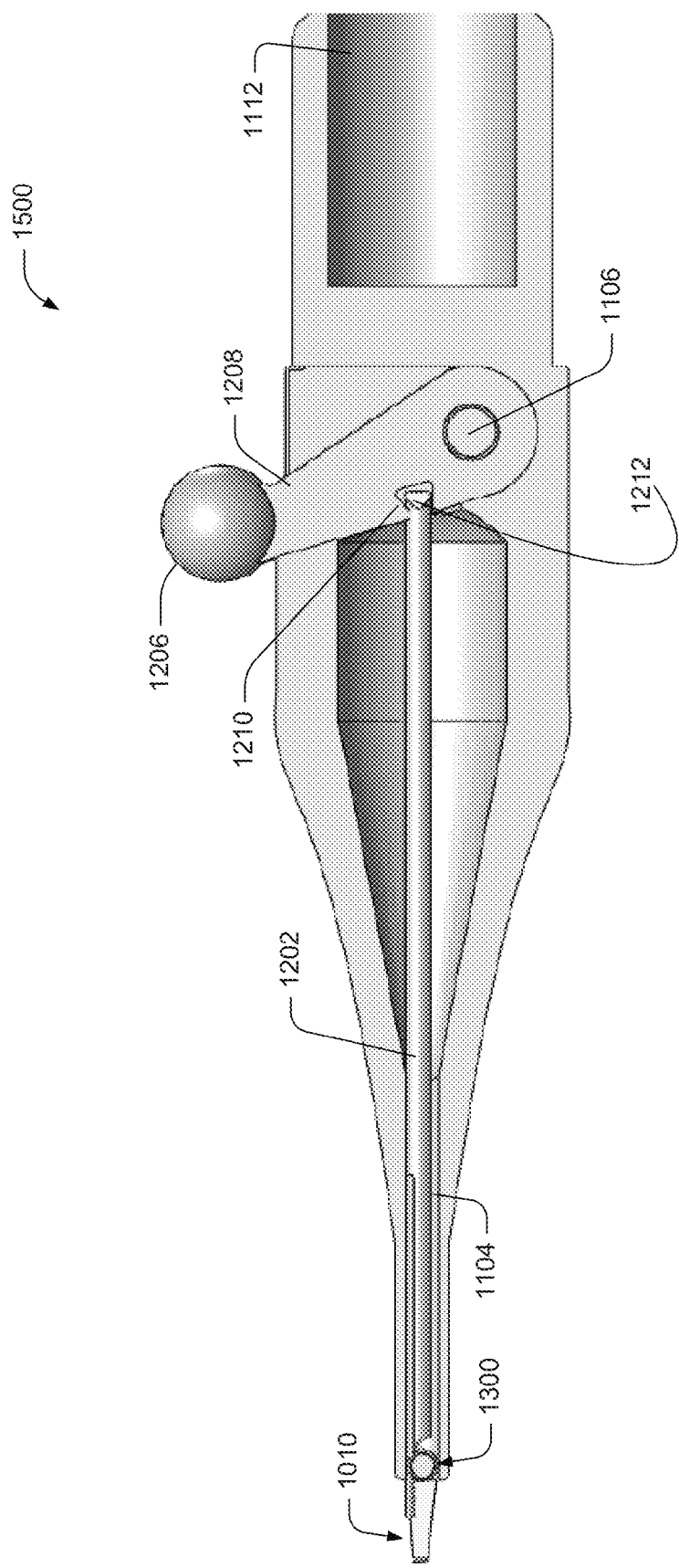
FIG. 16 shows a cut away view of the rack and pinion mechanism disposed within the device of FIG. 1.

Referring now to FIG. 16, as activation member 1208 rotates about pivot member 1106, shaft 1202 is caused to move laterally in channel 1104, thereby causing pinion 1300 to rotate cutting blade assembly 1010.

Figure 19:
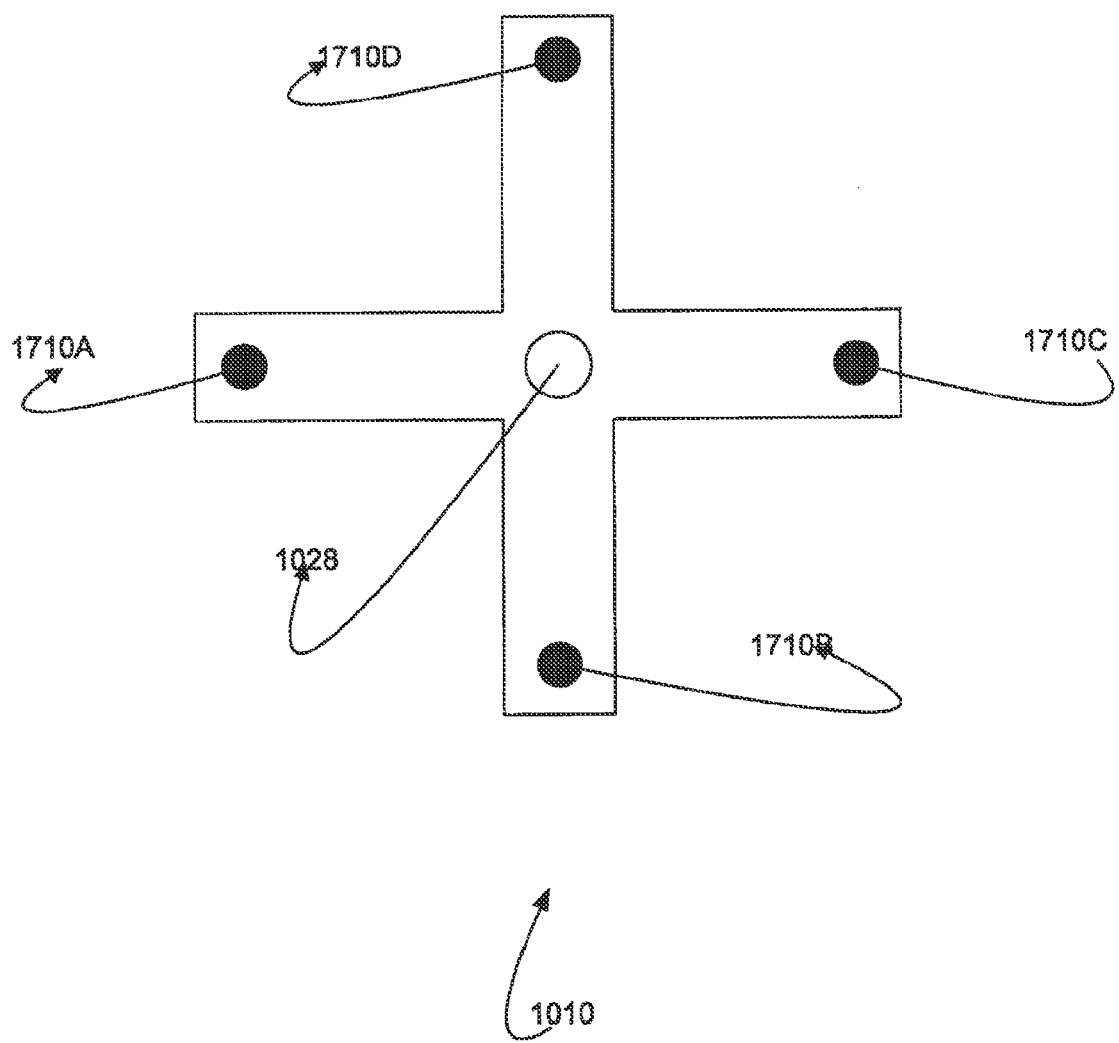
FIG. 19 shows a third embodiment of Applicants' cutting blade assembly.

Referring now to FIG. 19, in certain embodiments cutting blade assembly 1010 comprises four surgical blades, 1710A, 1710B, 1710C, and 1710D, wherein each surgical blade is disposed on an arm, wherein the arms extend outwardly from a center portion and are each offset by 90 degrees from the adjacent arms. In certain embodiments, the number and pitch of gear teeth 1310 and 1204 are selected such that the full linear movement of the shaft 1202 will result in rotational movement of the pinion by about 92 degrees. In certain embodiments, the number and pitch of gear teeth 1310 and 1204 are selected such that the full linear movement of shaft 1202 will result in rotational movement of the pinion by between about 90 and about 100 degrees.

Figure 18:
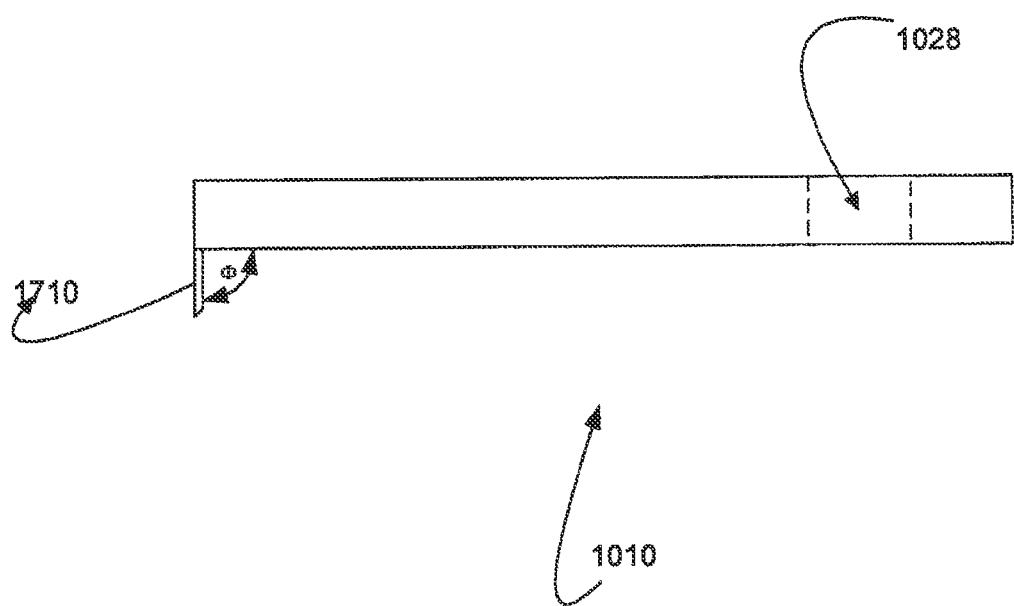
FIG. 18 shows a second embodiment of Applicants' cutting blade assembly.

Referring now to FIG. 18, in certain embodiments, blade assembly 1010 comprises a single surgical blade 1710. In these embodiments, the number and pitch of gear teeth 1310 and 1204 are selected such that the full linear movement of the rack assembly will result in rotational movement of the pinion by about 362 degrees.

Figure 17:
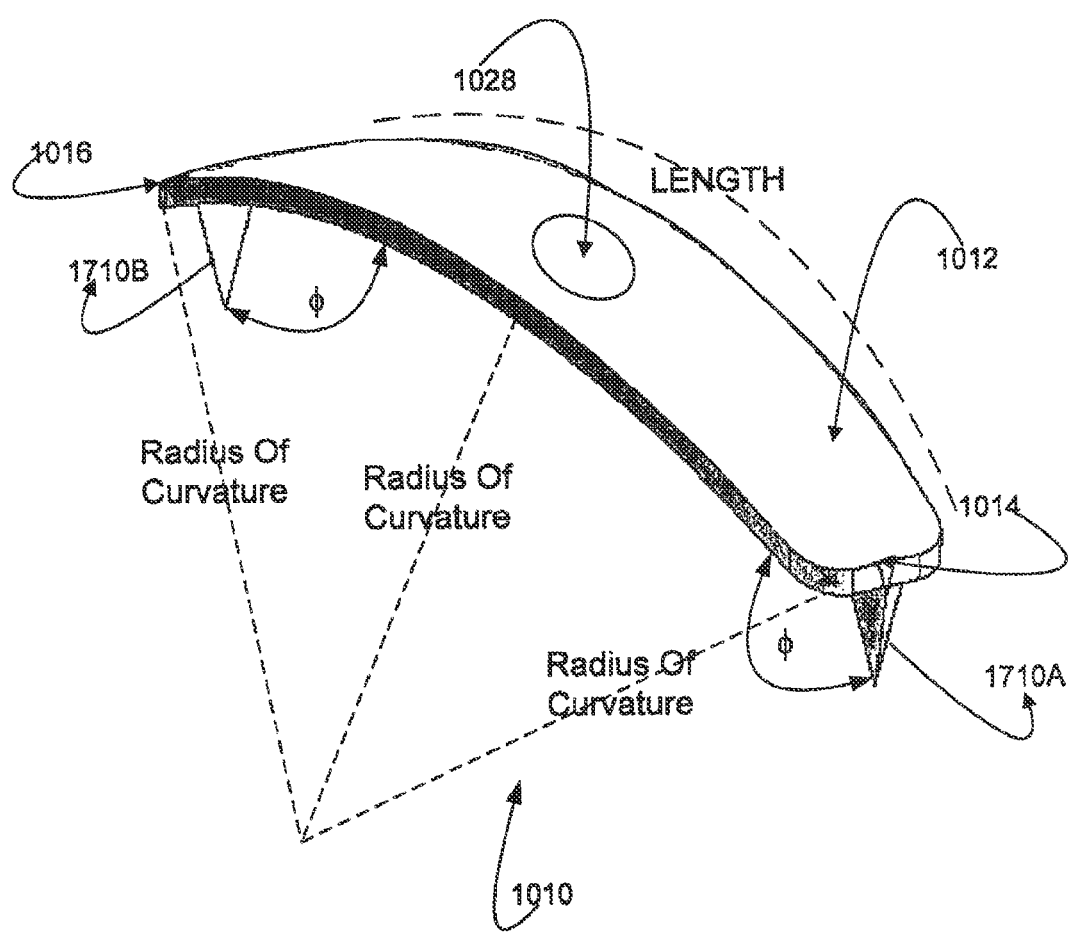
FIG. 17 shows one embodiment of Applicants' cutting blade assembly.

Referring now to FIG. 17, in certain embodiments, surgical blade 1710A and 1710B are angled relative to blade arm 1012, respectively. In certain embodiments, the angle is about 90 degrees. In certain embodiments, the angle is less than 90 degrees. In certain embodiments, the angle is greater than 90 degrees. In certain embodiments, surgical blades 1710A and 1710B each have two cutting edges that converge at an apex such that the blade assembly is capable of cutting in two rotational directions.

In certain embodiments, the blade arm 1012 is planar. FIG. 18 shows a planar blade arm 1012. In certain embodiments, the blade arm 1012 is curved such that the blade assembly 1010 forms an arcuate structure. FIG. 17 shows an arcuate blade arm 1012. In the illustrated embodiment of FIG. 17, blade arm 1012 comprise a radius of curvature. Further in the illustrated embodiment of FIG. 17, blade arm 1012 comprises a length. In certain embodiments, the radius of curvature substantially equals the length. By "substantially equals," Applicants mean the same dimension plus of minus about 10 percent. In certain embodiments, the radius of curvature does not substantially equal the length. In certain embodiments, the selection of a blade assembly 1010 with a particular radius of curvature is based on the dimensions of the patient's eye.

In certain embodiments, the surgical blades 1014 and 1016 extend away from blade arm 1012, respectively, such that the blades are parallel (i.e., the distance between the cutting edge of each blade is the same as the distance between the base of each blade). In certain embodiments, the surgical blades 1014 and 1016 extend away from blade arm 1012, respectively, at an inward angle (i.e., the distance between the cutting edge of each blade is closer than the distance between the base of each blade).

In certain embodiments, the blade assembly 1010 is held in place by mounting clips on the bottom portion of pinion 1300. In certain embodiments, the blade assembly 1010 is releaseably attached to the bottom portion of the pinion 1300 to enable the blade assembly 1010 to be exchanged or replaced.

In certain embodiments, the range of motion of the activator member 1208 within activator slot 1108 and the gear pitch on the shaft 1202 and the pinion 1300 is selected such that a full range of motion of the activator member 1208 will cause the blade assembly 1010 to rotate 182 degrees.

In certain embodiments, the shaft 1202 is flexible to allow the shaft to flex as the slot 1210 arcs around pivot member 1106.

In certain embodiments, the shaft 1202 is rigid and activator member 1208 is formed to include a vertical slot. The shaft 1202 is attached to the activator member 1208 by a pin that is disposed within the vertical slot. As the activator member 1208 is pivoted within the activator slot 1108, the pin travels up and down along the vertical slot, thereby allowing the shaft to remain straight while the shaft 1202 moves longitudinally within cavity 1104.

Figure 20:
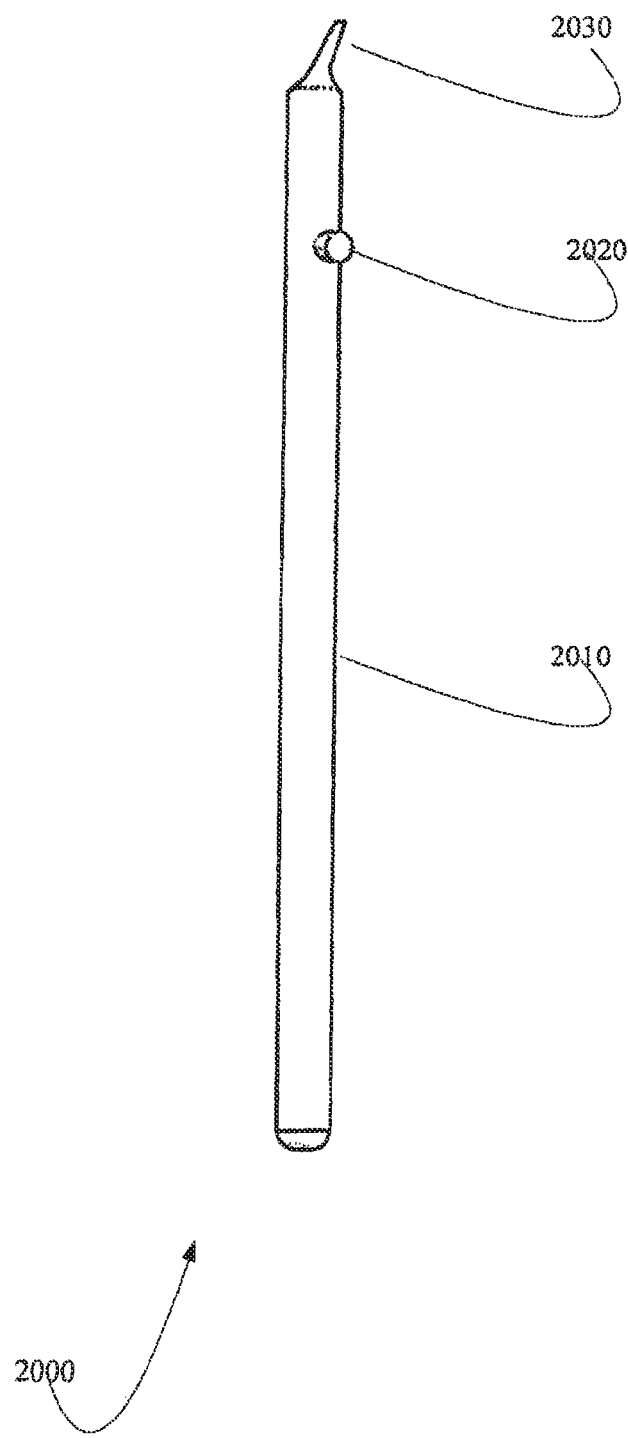
FIG. 20 shows a perspective view of Applicants' anterior capsulotomy device 2000.

FIG. 20 illustrates Applicants' Anterior Capsulotomy Device 2000. Device 2000 comprises body portion 2010, actuator 2020, and head portion 2030. In certain embodiments, head portion 2030 extends outwardly from body portion 2010 at an angle.

Figure 21A:
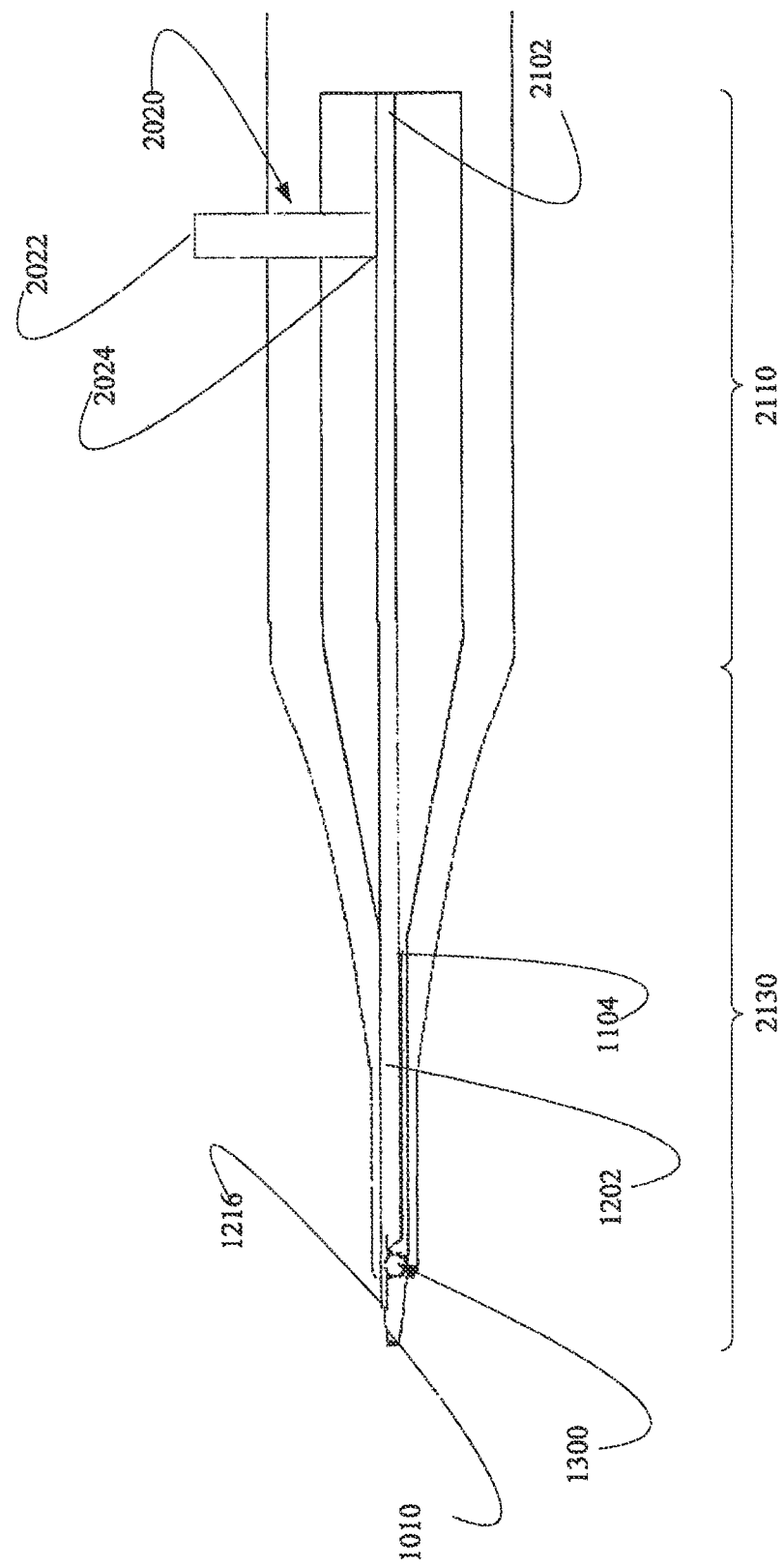
FIG. 21A shows a cross-section view of Applicants' anterior capsulotomy device 2100, wherein actuator 2020 is disposed in a first position.

Referring now to FIG. 21A, Applicants' Anterior Capsulotomy Device 2000 comprises an elastomeric, bendable, shaft 1202 (FIG. 12) comprising a distal end 1216 (FIG. 12) formed to include gear teeth 1204 (FIGS. 12A, 12B) disposed within body portion 2110 and extending into head portion 2130 via channel 1104. Gear teeth 1204 intermesh with gear teeth 1310 (FIGS. 13A, 13B) disposed on pinion 1300 (FIGS. 13A, 13B).

Referring once again to FIGS. 13A and 13B, pinion 1300 includes a blade assembly mounting member 1302. Blade assembly 1010 (FIG. 17) is attached to pinion 1300 by attaching blade assembly 1010 onto the blade assembly mounting member 1302

Referring once again to FIG. 21A, a first end 2022 of actuator 2020 extends outwardly from body portion 2110. A second end 2024 of actuator 2020 is disposed adjacent end 2102 of shaft 1202.

Referring to FIGS. 21A and 21B, FIG. 21A shows actuator 2020 in a first position, and distal portion 2102 of shaft 1202 in linear orientation. FIG. 21B shows actuator 2020 is a second position, and distal portion 2102 of shaft 1202 in a non-linear, i.e. arcuate, configuration. In the second position of FIG. 21B, first end 2022 is flush with the exterior of body portion 2110. Moving actuator 2020 from the first position of FIG. 21A to the second position of FIG. 21B causes actuator end 2024 to bend distal portion 1202 of shaft 1202 into the non-linear configuration of FIG. 21B.

Moving distal portion of shaft 1202 from the linear configuration of FIG. 21A to the non-linear configuration of FIG. 21B, moves distal end 1216 of shaft 1202 inwardly. Moving distal end 1216 inwardly causes pinion 1300 to rotate, and thereby rotates blade assembly 1010.

In certain embodiments wherein blade assembly 1010 comprises a single surgical blade 1710 as shown in FIG. 18, movement of actuator end 2022 from the first position of FIG. 21A to the second position of FIG. 21B, causes blade assembly 1010 to rotate about 362 degrees. In certain embodiments wherein blade assembly 1010 comprises two surgical blades 1710 as shown in FIG. 17, movement of actuator end 2022 from the first position of FIG. 21A to the second position of FIG. 21B, causes blade assembly 1010 to rotate about 182 degrees. In certain embodiments wherein blade assembly 1010 comprises four surgical blades 1710 as shown in FIG. 19, movement of actuator end 2022 from the first position of FIG. 21A to the second position of FIG. 21B, causes blade assembly 1010 to rotate about 92 degrees.

Figure 22A:
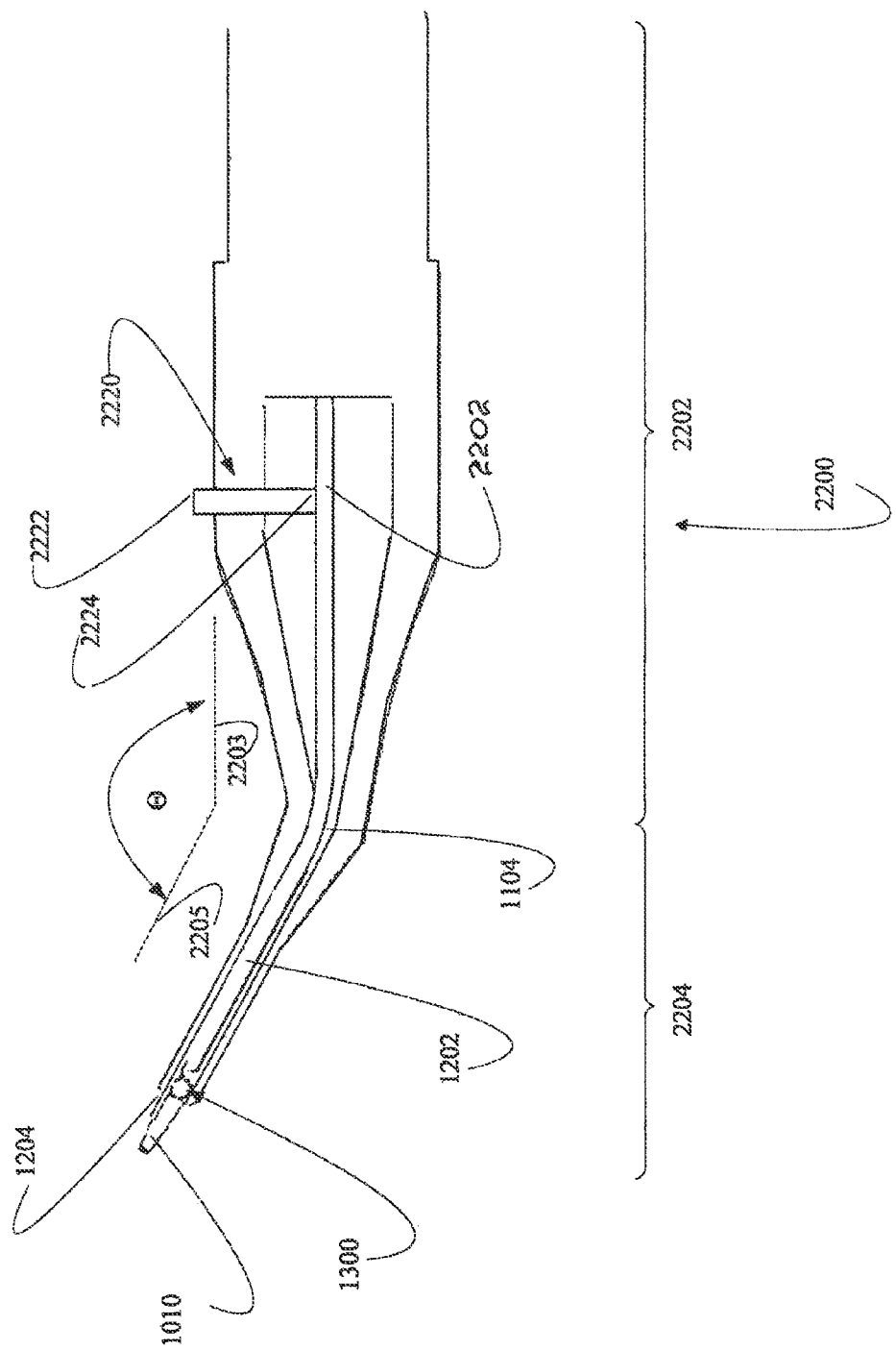
FIG. 22A shows a cross-section view of Applicants' anterior capsulotomy device 2200, wherein actuator 2020 is disposed in a first position.

Referring now to FIG. 22A, Applicants' Anterior Capsulotomy Device 2200 comprises a body portion 2210 and a head portion 2230. In the illustrated embodiment of FIG. 22A, a longitudinal axis 2203 of body portion 2210 is offset from a longitudinal axis 2205 of head portion 2230 by an angle Θ. In certain embodiments, angle Θ is between about 10 degrees and about 45 degrees. In certain embodiments, angle Θ is about 0 degrees.

Applicants' Anterior Capsulotomy Device 2200 further comprises shaft 1202 (FIG. 12) comprising a distal end 1216 (FIGS. 12A, 12B) formed to include gear teeth 1204 (FIGS. 12A, 12B) disposed within body portion 2210 and extending into head portion 2230 via channel 1104. Gear teeth 1204 intermesh with gear teeth 1310 (FIGS. 13A, 13B) disposed on pinion 1300 (FIGS. 13A, 13B).

Referring once again to FIGS. 13A and 13B, pinion 1300 includes a blade assembly mounting member 1302. Blade assembly 1010 (FIG. 17) is attached to pinion 1300 by attaching blade assembly 1010 onto the blade assembly mounting member 1302

Referring once again to FIG. 22A, a first end 2022 of actuator 2020 extends outwardly from body portion 2210. A second end 2024 of actuator 2020 is disposed adjacent end 2202 of shaft 1202.

Figure 22B:
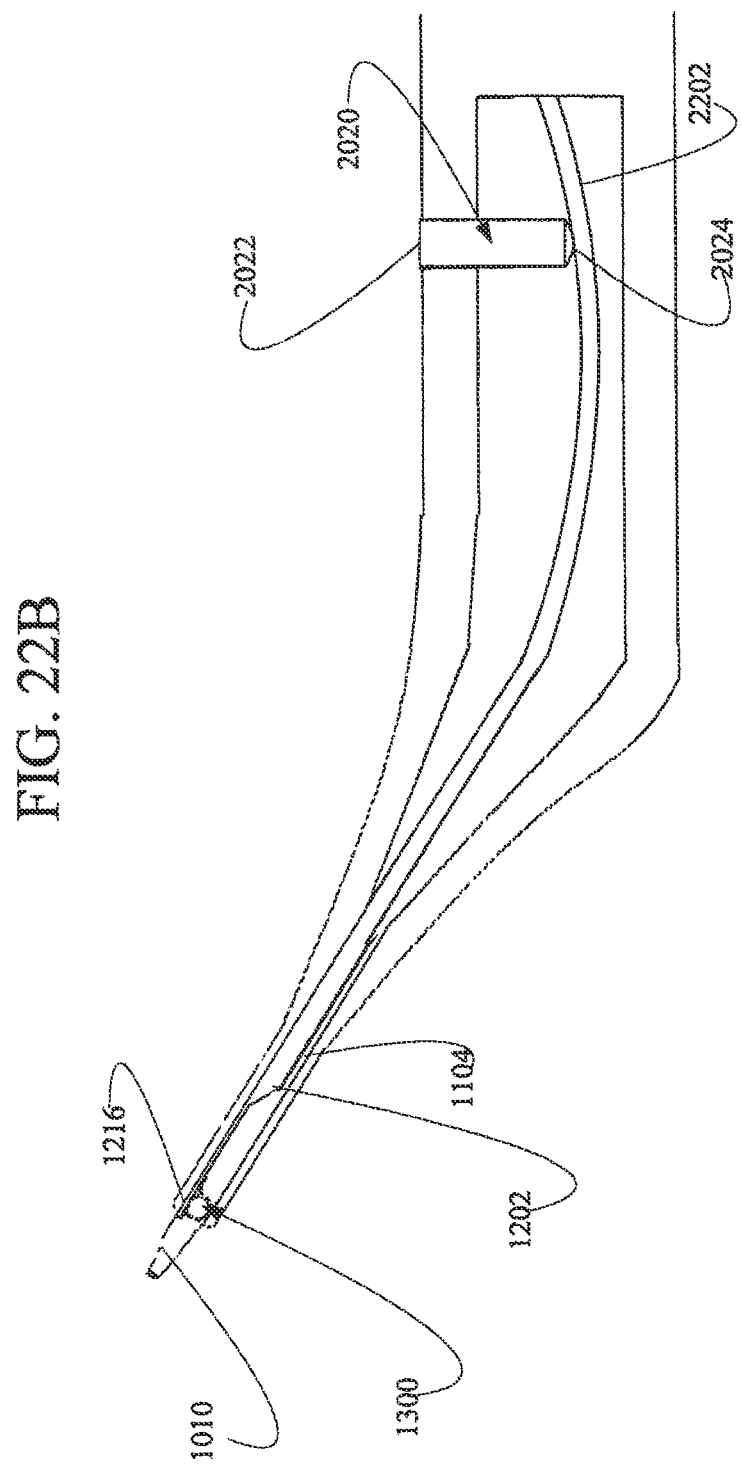
FIG. 22B shows a cross-section view of Applicants' anterior capsulotomy device 2100, wherein actuator 2020 is disposed in a second position.

Referring to FIGS. 22A and 22B, FIG. 22A shows actuator 2020 in a first position, and distal portion 2202 of shaft 1202 in linear orientation. FIG. 22B shows actuator 2020 in a second position, and distal portion 2202 of shaft 1202 in a non-linear, i.e. arcuate, configuration. In the second position of FIG. 22B, first end 2022 is flush with the exterior of body portion 2210. Moving actuator 2020 from the first position of FIG. 22A to the second position of FIG. 22B causes actuator end 2024 to bend distal portion 2202 of shaft 1202 into the non-linear configuration of FIG. 22B.

Moving distal portion of shaft 2202 from the linear configuration of FIG. 22A to the non-linear configuration of FIG. 22B, moves distal end 1216 of shaft 1202 inwardly. Moving distal end 1216 inwardly causes pinion 1300 to rotate, and thereby rotates blade assembly 1010.

In certain embodiments wherein blade assembly 1010 comprises a single surgical blade 1710 as shown in FIG. 18, movement of actuator end 2022 from the first position of FIG. 22A to the second position of FIG. 22B, causes blade assembly 1010 to rotate about 362 degrees. In certain embodiments wherein blade assembly 1010 comprises a two surgical blades 1710 as shown in FIG. 17, movement of actuator end 2022 from the first position of FIG. 22A to the second position of FIG. 22B, causes blade assembly 1010 to rotate about 182 degrees. In certain embodiments wherein blade assembly 1010 comprises four surgical blades 1710 as shown in FIG. 19, movement of actuator end 2022 from the first position of FIG. 22A to the second position of FIG. 22B, causes blade assembly 1010 to rotate about 92 degrees.

Figure 22C:
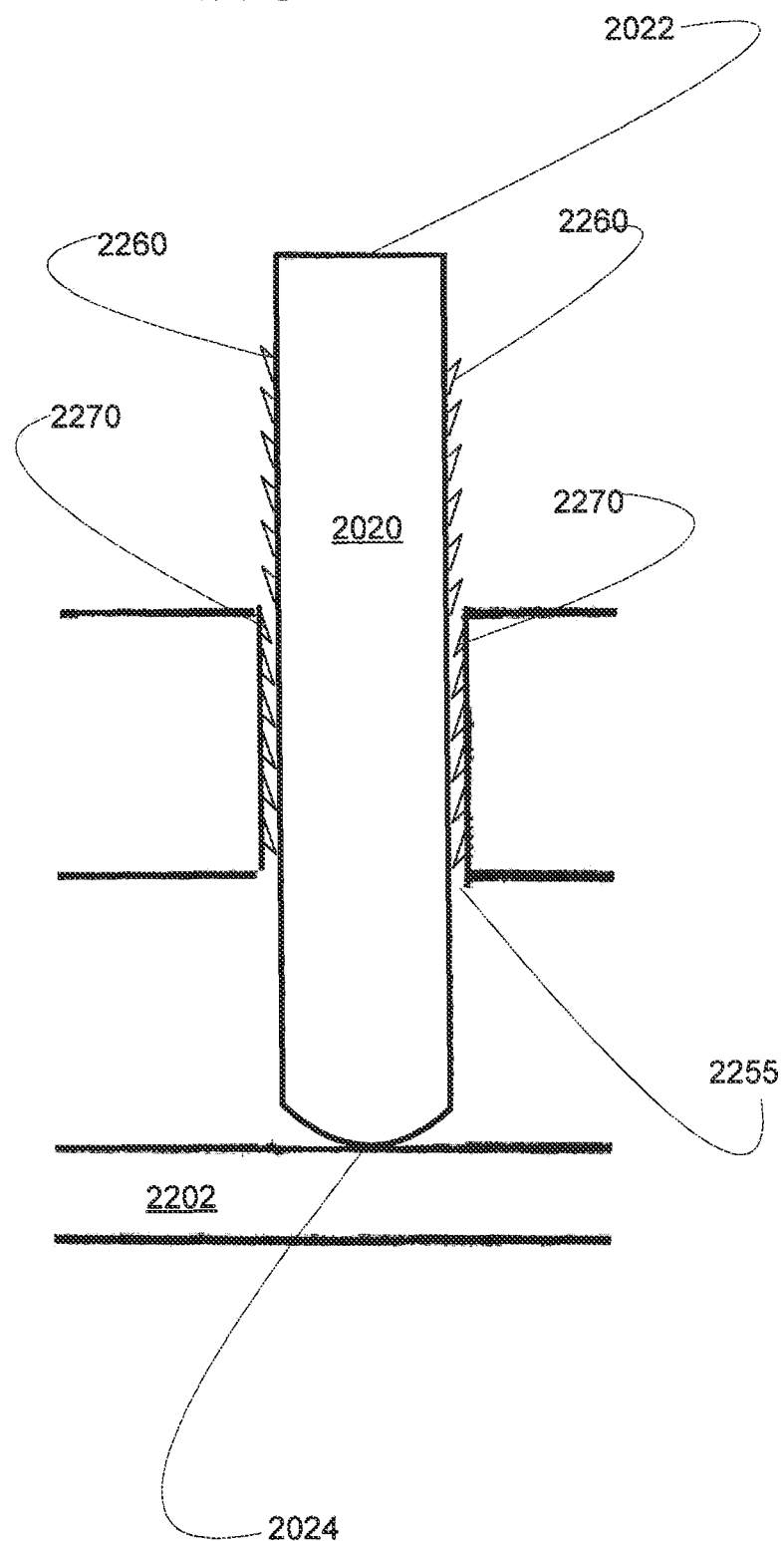
FIG. 22C shows a cross-section view of a first embodiment of Applicants' anterior capsulotomy device 2200, wherein actuator 2020 is configured to only permit a single use, wherein actuator 2020 is in a first position.

Referring now to FIG. 22C, body portion 2210 is formed to include a cylindrical aperture 2255 extending therethrough. Cylindrical aperture 2255 is defined by a cylindrical wall 2250. In certain embodiments, one or a plurality of downward-facing locking teeth 2270 are disposed on wall 2250.

Figure 22D:
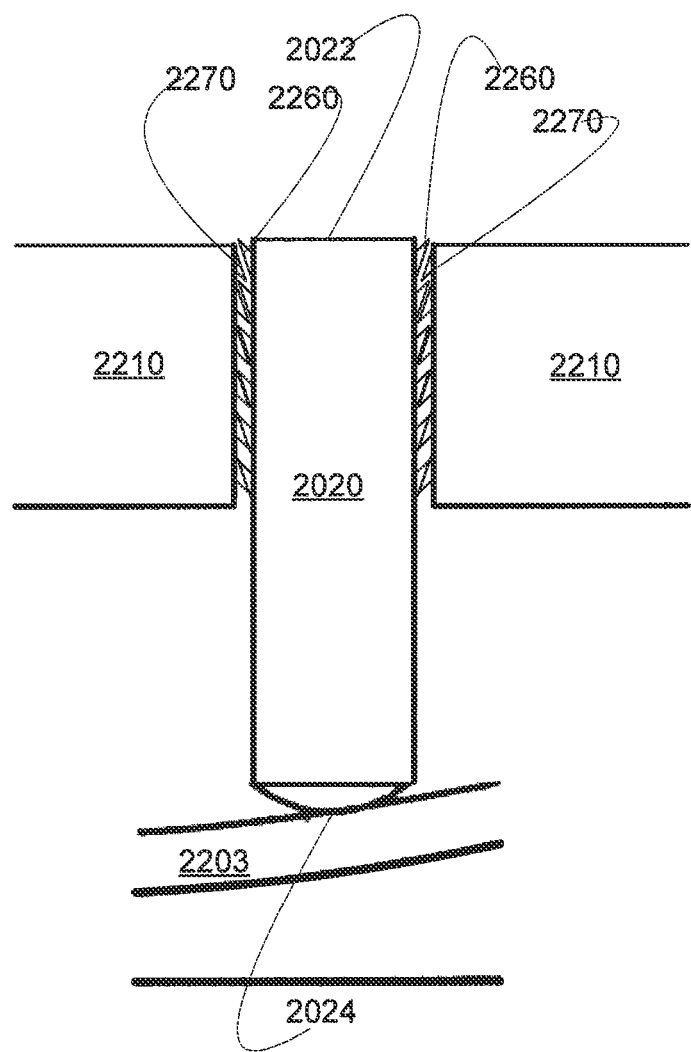
FIG. 22D shows a cross-section view of Applicants' anterior capsulotomy device 2200 of FIG. 22C, wherein actuator 2020 is configured to only permit a single use, wherein actuator 2020 is in a second and locked position.

In certain embodiments, actuator 2020 comprises a cylindrical assembly movably disposed within cylindrical aperture 2255. In the illustrated embodiment of FIG. 22C, one or a plurality of upward-facing locking teeth 2260 are disposed on a portion of cylindrical actuator 2020. The orientations of the one or a plurality of locking teeth 2260, and the orientations of the one or a plurality of locking teeth 2270, permit actuator 2022 to moved downwardly to cause rotation of blade assembly 1010 as described hereinabove. However, the orientations of the one or a plurality of locking teeth 2260, and the orientations of the one or a plurality of locking teeth 2270, do not permit movement of actuator 2020 from the second position of FIG. 22D back to the first Referring now to FIGS. 22C and 22D, when actuator 2020 is moved from the first position of FIG. 22C to the second position of FIG. 22D, the one or a plurality of locking teeth 2270 intermesh with the one or a plurality of locking teeth 2260 to prevent movement of actuator 2022 upwardly, i.e. from the second position of FIG. 22D to the first position of FIG. 22C. In the embodiments of FIGS. 22C and 22D, Applicants' Anterior Capsulotomy Device 2200 comprises a single use device.

Figure 23A:
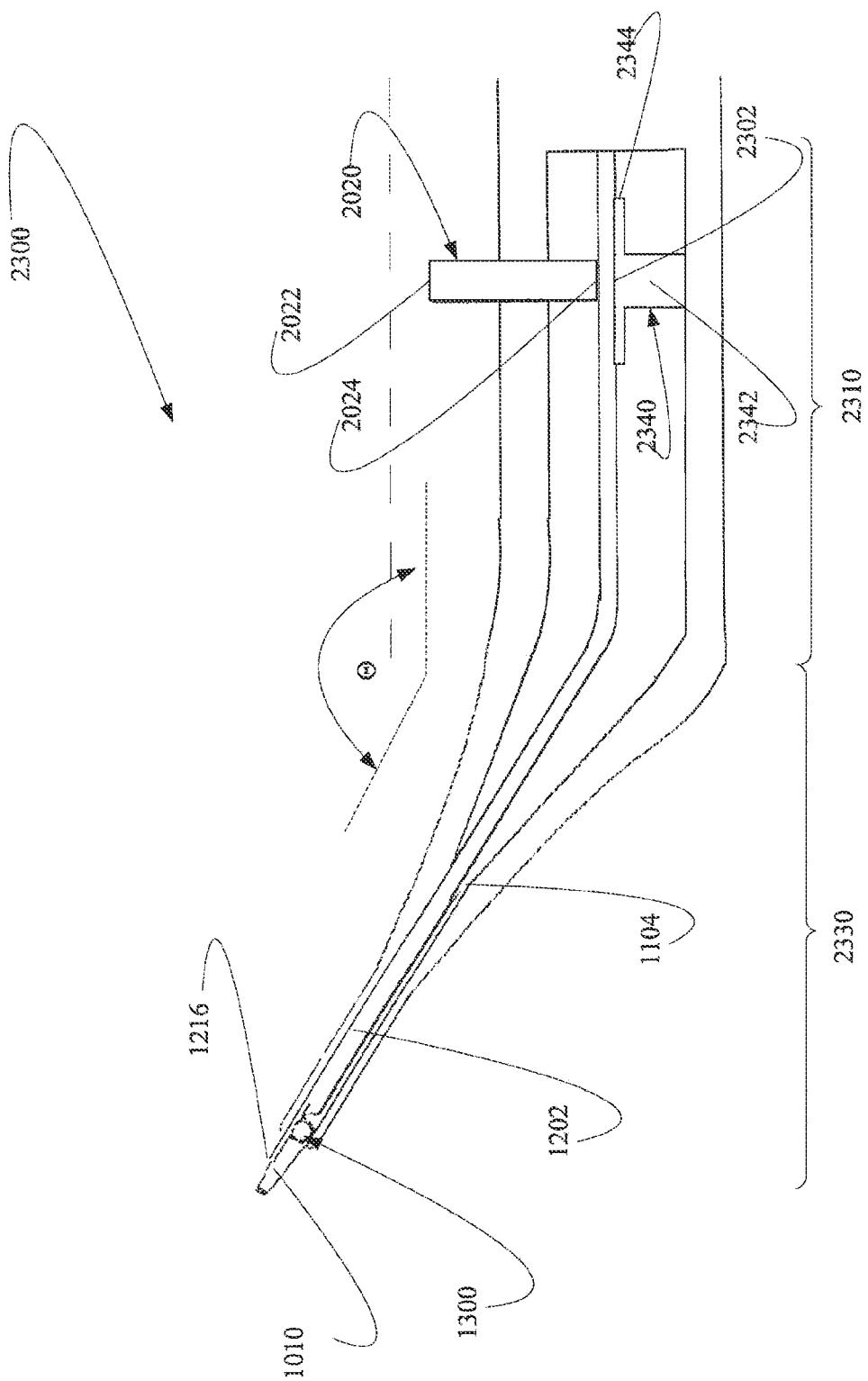
FIG. 23A shows a cross-section view of a second embodiment of Applicants' anterior capsulotomy device 2200, wherein actuator 2020 is configured to only permit a single use, wherein actuator 2020 is in a first position.
Figure 23B:
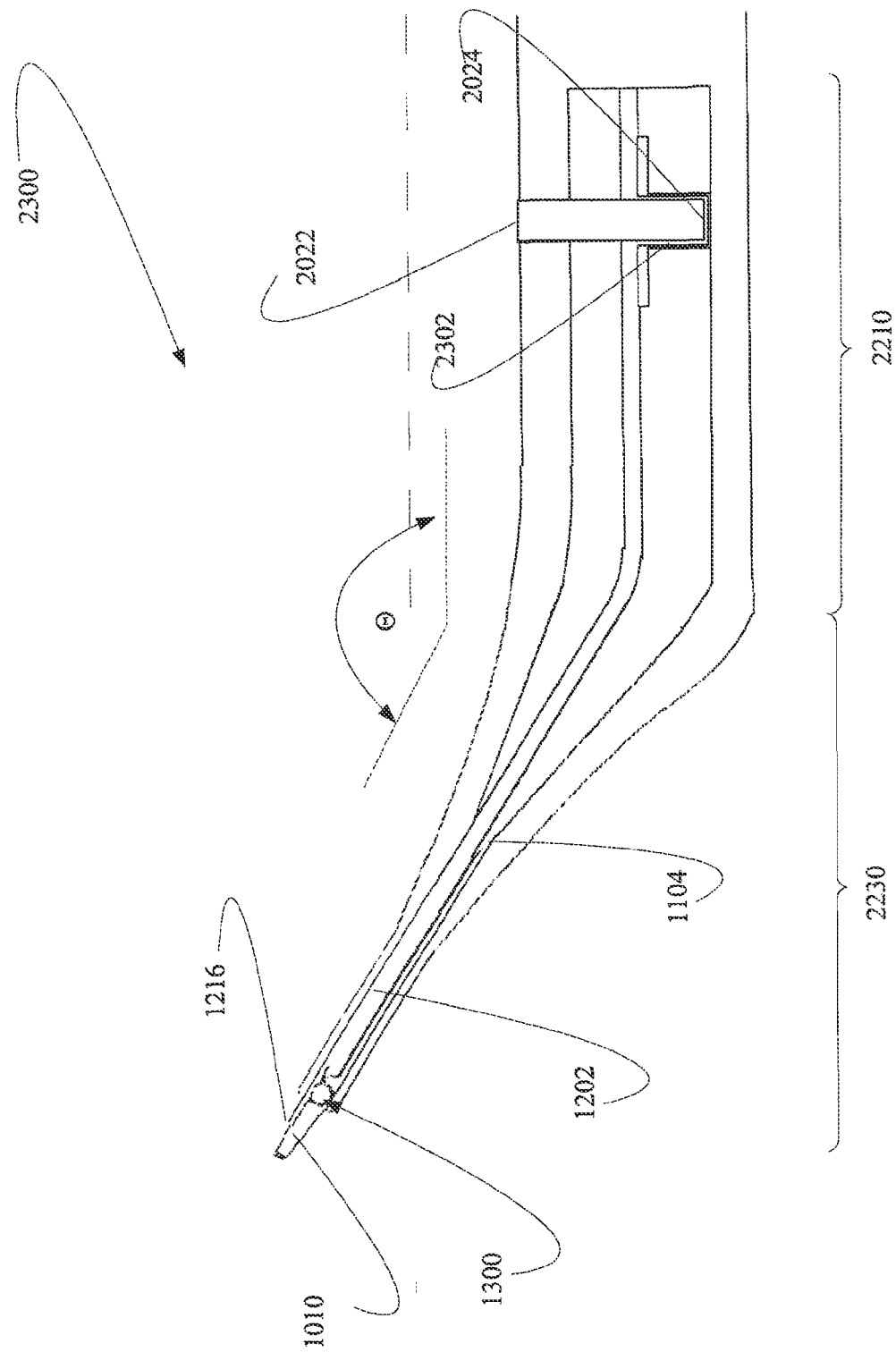
FIG. 23B shows a cross-section view of Applicants' anterior capsulotomy device 2200 of FIG. 23A, wherein actuator 2020 is configured to only permit a single use, wherein actuator 2020 is in a second and locked position.

Referring to FIG. 23B. in certain embodiments Applicants' Anterior Capsulotomy Device 2300 distal end 2302 of shaft 1202 is disposed across a top portion of assembly 2340. Assembly 2340 comprises a cylindrical shape and is formed to include a bore 2342 therein. Assembly 2340 further comprises an annular lip 2344 defining an opening to bore 2342. When actuator 2020 is disposed in a first position illustrated in FIG. 23A, end portion 2024 is disposed on distal portion 2302 of shaft 1202, and distal portion 2302 is disposed on lip 2344 and spans the opening to bore 2340.

Referring to FIGS. 23A and 23B, when actuator 2020 is moved from the first position of FIG. 23A to the second position of FIG. 23B, distal portion of shaft 1202 is extruded into bore 2340 by end 2024, thereby moving distal end 1216 of shaft 1202 inwardly. Moving distal end 1216 inwardly causes pinion 1300 to rotate, and thereby rotates blade assembly 1010.

In certain embodiments wherein blade assembly 1010 comprises a single surgical blade 1710 as shown in FIG. 18, movement of actuator end 2022 from the first position of FIG. 23A to the second position of FIG. 23B, causes blade assembly 1010 to rotate about 362 degrees. In certain embodiments wherein blade assembly 1010 comprises a two surgical blades 1710 as shown in FIG. 17, movement of actuator end 2022 from the first position of FIG. 23A to the second position of FIG. 23B, causes blade assembly 1010 to rotate about 182 degrees. In certain embodiments wherein blade assembly 1010 comprises four surgical blades 1710 as shown in FIG. 19, movement of actuator end 2022 from the first position of FIG. 23A to the second position of FIG. 23B, causes blade assembly 1010 to rotate about 92 degrees.

In certain embodiments, shaft 1202 is formed from a non-elastomer. In certain embodiments, that non-elastomer is a metallic strip. In embodiments, wherein shaft 1202 is formed from a non-elastomer, the deformation made by extruding distal end 2302 into bore 2340 is permanent. In these embodiments, after being extruded into bore 2340 shaft 1202 cannot return to its original, substantially linear configuration of FIG. 23A. In these embodiments, Applicants' Anterior Capsulotomy Device 2200 comprises a single use device.

While the preferred embodiments of the present invention have been illustrated in detail, it should be apparent that modifications and adaptations to those embodiments may occur to one skilled in the art without departing from the scope of the present invention.

We claim:

1. A device for performing an anterior capsulotomy procedure, comprising: a body comprising an arm attached to and extending outwardly from a first end of a handle portion, and formed to include an arm cavity formed in said arm, an activation slot formed through a side of said handle portion and in communication with said arm cavity, a pivot member integrally formed within said activation slot, and a handle cavity extending through a second end of said handle, wherein said arm cavity and said activation slot are not located within said handle cavity; a rotatable cutting element; a pinion rotatably attached to and extending outwardly from said body and having a circumference, wherein said arcuate member is attached to a distal end of said pinion; a first set of gear teeth disposed around a portion of said circumference; a shaft slideably disposed within said arm cavity and comprising a distal end and a proximal end, wherein: said shaft is moveable between a forward position and a rearward position; a second set of gear teeth disposed along said distal end of said shaft, wherein said first set of gear teeth intermesh with said second set of gear teeth; an actuator attached to a distal end of said shaft and extending outwardly from said handle portion through said activation slot, wherein the actuator is movable between a first actuator position and a second actuator position; wherein when said actuator is moved from said first actuator position to said second actuator position said shaft moves from said forward position to said rearward position causing said pinion to rotate said arcuate member.

2. The device of claim 1, wherein said rotatable cutting element comprises:

a plurality of surgical blades and an arcuate member, wherein the arcuate member has a first end, a second end, a first surface, and a second surface, wherein the first end of the arcuate member opposes the second end of the arcuate member, wherein the first surface opposes the second surface, wherein a first surgical blade is attached to the first end of the arcuate member and extends outwardly therefrom.

3. The device of claim 2, wherein the arcuate member can be rotated about 362 degrees.

4. The device of claim 2, wherein a second surgical blade is attached to the second end of the arcuate member and extends outwardly there from.

5. The device of claim 4, wherein the arcuate member can be rotated about 182 degrees.

6. The device of claim 1, wherein the actuator is manually operated.

7. The device of claim 1, wherein the device can only be used a single time.

8. The device of claim 1, wherein said shaft comprises a bendable elastomer.

9. The device of claim 1, wherein said shaft comprises a metal strip.

10. A method of performing an anterior capsulotomy, the method comprising: making an incision in an eye; providing a device comprising: a body comprising an arm attached to and extending outwardly from a first end of a handle portion, and formed to include an arm cavity formed therein, an activation slot formed through a side of said handle portion and in communication with said arm cavity, a pivot member integrally formed within said activation slot, and a handle cavity extending through a second end of said handle, wherein said arm cavity and said activation slot are not located within said handle cavity; a rotatable cutting element; a pinion rotatably attached to and extending outwardly from said body and having a circumference, wherein said arcuate member is attached to a distal end of said pinion; a first set of gear teeth disposed around a portion of said circumference; a shaft slideably disposed within said arm cavity and comprising a distal end and a proximal end, wherein said shaft is moveable between a forward position and a rearward position; a second set of gear teeth disposed along said distal end of said shaft, wherein said first set of gear teeth intermesh with said second set of gear teeth; an actuator attached to a proximal end of said shaft and attached to said pivot member and extending outwardly from said handle portion through said activation slot, wherein the actuator is movable between a first actuator position and a second actuator position; wherein when said actuator is moved from said first actuator position to said second actuator position said shaft moves from said forward position to said rearward position causing said pinion to rotate said arcuate member. inserting a portion of said rotatable cutting element into the incision; and transforming the anterior capsule wall by moving the actuator from the first actuator position to the second actuator position to create an aperture there through.

11. The method of claim 10, wherein said rotatable cutting element comprises:
a plurality of surgical blades and an arcuate member, wherein the arcuate member has a first end, a second end, a first surface, and a second surface, wherein the first end of the arcuate member opposes the second end of the arcuate member, wherein the first surface opposes the second surface, wherein a first surgical blade is attached to the first end of the arcuate member and extends outwardly therefrom.

12. The method of claim 11, wherein the arcuate member can be rotated about 362 degrees.

13. The method of claim 10, wherein a second surgical blade is attached to the second end of the arcuate member and extends outwardly there from.

14. The method of claim 13, wherein the arcuate member can be rotated about 182 degrees.

15. The method of claim 10, wherein said shaft comprises a bendable elastomer.

16. The method of claim 10, wherein said shaft comprises a metal strip.

17. The method of claim 10, further comprises disposing of said device after a single use.

* * * * *